(12) United States Patent
Baron et al.

(10) Patent No.: US 6,916,603 B2
(45) Date of Patent: Jul. 12, 2005

(54) METHODS OF USING AGENTS THAT MODULATE BONE FORMATION AND INHIBIT ADIPOGENESIS

(75) Inventors: Roland E. Baron, Guilford, CT (US); Natalie Sims, Fitzroy (AU); Georgios Sabatakos, New Haven, CT (US); Eric Nestler, Dallas, TX (US); Jingshan Chen, Cheshire, CT (US); Max Kelz, Penn Valley, PA (US)

(73) Assignee: Yale University, New Haven, CT (US)

( * ) Notice: Subject to any disclaimer, the term of this patent is extended or adjusted under 35 U.S.C. 154(b) by 180 days.

(21) Appl. No.: 09/939,709

(22) Filed: Aug. 28, 2001

(65) Prior Publication Data

US 2002/0077273 A1 Jun. 20, 2002

Related U.S. Application Data

(60) Provisional application No. 60/228,450, filed on Aug. 29, 2000.

(51) Int. Cl.$^7$ ............................ C12Q 1/00; C12Q 1/68; C12N 15/63; C12N 15/74; C07H 21/04
(52) U.S. Cl. ............................... 435/4; 435/6; 435/7.1; 435/320.1; 435/455; 536/23.1; 536/23.2; 536/24.1
(58) Field of Search ...................... 435/4, 6, 7.1, 320.1, 435/455, 377, 93.2; 536/23.1, 24.1, 23.2; 800/3, 21

(56) References Cited

U.S. PATENT DOCUMENTS 6,653,064 B1 * 11/2003 Jochum et al. ................ 435/4

OTHER PUBLICATIONS

Agamemnon et al., J Cell Biol 122:685–701, 1993.*
Gruda et al. Oncogene 12(10) abstract only, May 1996.*
Chen, J. et al., Transgenic animals with inducible, targeted gene expression in brain. *Mol. Pharmacol.* 54, 495–503 (1998).
Chen, J. et al., Chronic Fos–related antigens: stable variants of ΔFosB induced in brain by chronic treatments. *J Neurosci* 17, 4933–4941 (1997).
Grigoriadis, A. et al., Osteoblasts are target cells for transformation in c–fos Transgenic Mice. *The Journal of Cell Biology* 122, 685–701 (1993).
Gruda, M. C. et al., Expression of FosB during mouse development: normal development of FosB knockout mice. *Oncogene* 12, 2177–2185 (1996).
International Search Report.
Kelz, M.B. et al., Expression of the transcription factor ΔFosB in the brain controls sensitivity to cocaine. *Nature* 401, 272–276 (1999).
Lee, K. et al., Parathyroid hormone induces a sequential c–fos expression in bone cells in vivo: *in situ* localization of its receptor and c–fos messenger ribonucleic acids. (Abstract) *Endocrinology* 134 (1), 441–450 (1994).
Mathieu E. et al, Establishment of an osteogenic cell line derived from adult mouse bone marrow stroma by use of a recombinant retrovirus, *Calcif Tissue Int* 50, 362–371 (1992).
Nakabeppu, Y. et al., A naturally occurring truncated form of FosB that inhibits Fos/Jun transcriptional activity. *Cell* 64, 751–759 (1991).
Nestler, E. J. et al., DeltaFosB: a molecular mediator of long–term neural and behavioral plasticity. *Brain Research* 835, 10–17 (1999).
Owen, T. A., et al., Coordinate occupancy of AP–1 sites in the vitamin D–responsive and CCAAT box elements by Fos–Jun in the osteocalcin gene: Model for phenotype suppression of transcription. *Proc Natl Acad Sci U S A* 87, 9990–9994 (1990).
Sabatakos, G., Overexpression of ΔFosB transcription factor(s) increases bone formation and inhibits adipogenesis. Nature Medicine 6 (8), 985–990 (2000).
Weitzman, J., Bone Fos–silization. *TRENDS in Molecular Medicine*, 7 (1), 10 (2001).

* cited by examiner

*Primary Examiner*—Joseph Woitach
(74) *Attorney, Agent, or Firm*—Morgan, Lewis & Bockius LLP

(57) ABSTRACT

The present invention is based on the discovery that overexpression of ΔFosB leads to bone formation and that ΔFosB expression inhibits adipogenesis. The present invention provides methods of identifying agents that modulate bone formation and adipogenesis. Moreover, the present invention provides methods for identifying genes that are modulated by ΔFosB and that modulates ΔFosB, osteogenesis, and adipogenesis.

22 Claims, 5 Drawing Sheets

METHODS OF USING AGENTS THAT MODULATE BONE FORMATION AND INHIBIT ADIPOGENESIS

RELATED APPLICATIONS

This application claims the benefit of U.S. Provisional Application 60/228,450, filed Aug. 29, 2000, which is herein incorporated by reference in its entirety.

FIELD OF THE INVENTION

The present invention relates to methods of identifying agents that modulate ΔFosB expression. Specifically, the present invention relates to identifying agents that modulate osteogenesis and adipogenesis. The present invention also relates to methods of identifying genes modulated by ΔFosB or modulates ΔFosB expression and associated with osteogenesis and adipogenesis. Additionally, the present invention relates to using the identified agents to treat subjects with diseases or conditions associated with abnormal bone formation and abnormal adipogenesis.

BACKGROUND

Bone Formation

Bone formation, i.e. osteogenesis, is essential for the maintenance of bone mass in the adult skeleton. It begins during prenatal development and persists throughout adulthood. There are two ways in which osteogenesis occurs: intramembranous ossification and endochondral ossification.

There are two types of cells that are important in osteogenesis. Osteoblasts, involved in both endochondral and intramembranous ossification, are the specialized cells in bone tissue that make matrix proteins resulting in the formation of new bone. These bone-forming cells are derived from mesenchymal osteoprogenitor cells. They form an osseous matrix in which they become enclosed as an osteocyte. They are capable of differentiating to other lineages such as adipocytes, chondrocytes and muscle (Bellows et al., 1994). Unlike osteoblasts, osteoclasts are used in endochondral ossification. They dissolve calcium previously stored away in bone and carry it to tissues whenever needed. Thus, while osteoblasts are associated with new bone growth, osteoclasts are associated with bone absorption and removal.

Bone is subject to constant breakdown and resynthesis in a complex process mediated by osteoblasts, which produce new bone, and osteoclasts, which destroy bones. In normal bone, the balance between osteoblast-mediated bone formation and osteoclast-mediated bone resorption is maintained through complex regulating interactions.

Conditions and Diseases Associated with Bone Formation

There are many deficiencies, diseases, and disorders associated with the skeletal system. Examples of a few include, but are not limited to, osteoporosis, bone cancer, arthritis, rickets, bone fracture, periodontal disease, bone segmental defects, osteolytic bone disease, primary and secondary hyperparathyroidism, Paget's disease, osteomalacia, hyperostosis, and osteopetrosis.

Accordingly, there is a need to develop methods of treating diseases associated with bone growth disorders, methods of hastening bone formation, methods of identifying agents that modulate (increase or decrease) bone formation, and methods of identifying genes associated with bone growth disorders.

ΔFosB

The AP-1 family of transcription factors consists of dimeric complexes of Fos-related (c-Fos, FosB, ΔFosB, Fra-1 and Fra-2) and Jun-related (cJun, JunB and JunD) proteins. These are basic leucine zipper proteins that modulate the transcription of a variety of genes via interactions with specific sequences on the promoters of target genes. Members of the AP-1 family participate in the regulation of bone cell proliferation and differentiation, and the promoters of several genes involved in bone formation contain AP-1 consensus sequences. In addition, several regulators of bone formation induce AP-1 expression in early osteoblast precursors (Grigoriades et al., 1993). Furthermore, mice overexpressing c-Fos develop osteosarcomas (Grigoriades et al., 1993, Wang et al., 1992) while c-fos knockout mice lack osteoclasts and develop osteopetrosis (Johnson et al., 1992; Wang et al., 1992). In contrast, no bone abnormalities have been described in fosB knockout mice (Gruda et al., 1996), nor in mice where FosB, Fra-2, c-Jun or JunB alone were overexpressed (Grigoriadis et al., 1993).

Despite numerous studies on the role of AP-1 family members in skeletal biology, the role of ΔFosB, a Fos-related protein that arises from alternative splicing of the fosB transcript, has never been analyzed. ΔFosB can be induced in a region-specific manner in brain in response to several types of chronic perturbation, including drugs of abuse, antipsychotic drugs, antidepressant drugs, seizures and lesions (Chen et al., 1998). Once induced, ΔFosB isoforms persist in brain for relatively long periods due to their extraordinary stability. Mice lacking the fosB gene show abnormal biochemical and behavioral responses to chronic administration of drugs of abuse or antidepressant treatments, consistent with an important role for ΔFosB in mediating long-term adaptations in the brain (Nestler et al., 1999).

The Relationship Between Adipogenesis and Osteogenesis

Adipocytes form an integral part of the stromal system of bone and marrow and participate in the establishment and maintenance of the hematopoietic microenviroment (Beresford et al, 1992). Adipocytic and osteogenic cells are the two main cell lines of the marrow stromal system. There is also evidence that they are derived from a multipotential stromal stem cell in the adult marrow (Beresford et al, 1992). Beresford et al. (1992) report that there is evidence for an inverse relationship between the expression of the adipocytic and osteogenic phenotypes in cultures of rat marrow stromal cells. Beresford et al. (1992) also report that this finding is consistent with the possibility that the regulation of adipogenesis and osteogenesis can occur at the level of a common precursor.

Gimble et al. (1995) describe the effects of bone morphogenetic proteins on adipogenesis in a multipotent murine bone marrow stromal cell line, BMS2 Gimble et al. (1995) report that bone morphogenetic proteins inhibit adipocyte differentiation in multipotent bone marrow stromal cells in vitro.

Diseases Associated with Adipogenesis

Diseases associated with adipogenesis include body weight disorders such as obesity, anorexia, cachexia, and nonshivering and shivering thermogenesis. Obesity is usually defined as body weight of more than 20% in excess of the ideal body weight. Obesity is associated with an increased risk for cardiovascular disease, diabetes, and an increased mortality rate (Grundy et al., 1990, Disease-a-Month 36:645–696). On the other hand, loss of appetite, diminished food intake, and loss of body weight are also problems associated with many diseases.

Thus, there is also a need to develop methods of treating diseases associated with adipogenesis, methods of identifying agents that modulate adipogenesis, and methods of identifying genes associated with adipogenesis.

SUMMARY OF THE INVENTION

The present invention provides a method of identifying an agent that modulates bone formation or osteogenesis. Preferably, this method is practiced by administration of a test agent, and monitoring expression of ΔFosB to determine whether the agent modulates bone formation, wherein an increase in the expression of ΔFosB indicates that the agent is an inducer of bone formation and wherein a decrease in the expression of ΔFosB indicates that the agent is an inhibitor of bone formation.

The present invention also provides a method of identifying an agent that interacts with ΔFosB comprising incubating a test agent with ΔFosB and detecting an interaction between ΔFosB and the test agent.

In one embodiment of the invention, the agent is administered to isolated cells in culture, such as, but not limited to, osteoblasts and chondrocytes, preferably, primary osteoblasts, MC3T3-E1 cells, or C2C12 cells. In another embodiment, the agent is administered to cell lysates, specifically nuclear extracts. In a third embodiment of the invention, the agent is administered to a non-human transgenic animal, preferably mice and most preferably mice that overexpress ΔFosB.

The present invention also provides a method of identifying an agent that modulates adipogenesis. Preferably, this method is practiced by administration of a test agent and monitoring expression of ΔFosB to determine whether the agent modulates adipogenesis, wherein an increase in the expression of ΔFosB indicates that the agent is an inhibitor of adipogenesis and wherein a decrease in the expression of ΔFosB indicates that the agent is an inducer of adipogenesis.

In one embodiment of the invention, the agent is administered to isolated cells in culture, such as, but not limited to, primary adipocytes, 3T3-L1 preadipocytes, 3T3 F422A, and ob 1771. In another embodiment, the agent is administered to cell lysates, specifically nuclear extracts. In a third embodiment of the invention, the agent is administered to a non-human transgenic animal, preferably mice and most preferably mice that overexpress ΔFosB.

Alternatively, the methods of the present invention may be practiced using a yeast two hybrid system or reporter gene system to monitor the expression of ΔFosB.

Moreover, the present invention provides a method of modulating the differentiation or proliferation of cells including but not limited to osteoblast, bone marrow stromal cells, or pluripotent precursor cells by administering an agent that modulates bone formation or ΔFosB expression.

In one aspect, the present invention contemplates a method of modulating differentiation or proliferation of cells including but not limited to adipocytes, preadipocytes, bone marrow stromal cells, or pluripotent precursor cells by administering an agent that modulates adipogenesis or ΔFosB expression.

In another aspect, the present invention contemplates using agents identified to modulate bone formation or adipogenesis for treating diseases associated with osteogenesis or adipogenesis. These diseases include but are not limited to osteoporosis, bone cancer, arthritis, rickets, bone fracture, periodontal disease, bone segmental defects, osteolytic bone disease, primary and secondary hyperparathyroidism, Paget's disease, osteomalacia, hyperostosis, osteopetrosis, osteosclerosis, osteoporosis, obesity, anorexia, cachexia, and nonshivering and shivering thermogenesis.

Further, the present invention provides a method of identifying genes that are modulated by ΔFosB comprising inducing ΔFosB in a cell and determining which genes are differentially expressed, thereby identifying genes that are modulated by ΔFosB or associated with ΔfosB mediating its action on bone formation or adipogenesis. Preferably, this method is performed using a yeast two-hybrid system or hybridization of cellular nucleic acids to a DNA chip, for example, to be used in target identification.

The present invention also provides a method of identifying genes that modulate ΔFosB expression comprising measuring the expression level of ΔFosB in the presence of test genes, thereby identifying genes that modulate ΔFosB. The test genes may originate from a nucleic acid library and the test genes may be present on a heterologous vector. The expression level of ΔFosB may be determined by using Northern blot analysis, Western blot analysis, PCR analysis, or two hybrid screening assays, or a reporter gene system. The contemplated reporter gene system may comprise a reporter gene linked to a promoter that interacts with ΔFosB. Additionally, the method comprises ΔFosB linked to a heterologous protein. The method may be performed using a cell based or cell free system. Further, the method may be performed using high throughput assays using, for example, DNA chip.

A. Contact radiograph of 15 week old control (left) and 1A ΔFosB littermates (right). B. Schematic diagram of the functional domains of FosB and ΔFosB (upper panel): FHD: Fos-homology domain, BR: basic region, LZ: leucine zipper, PPP: proline-rich transactivation domain. In vitro transcription/translation of ΔFosB (Δ) or of mutants lacking the first (Δ1) or the first and second (Δ2) methionine residues (bottom panel) (Chen et al., 1997). C. Tissue-specific expression of ΔFosB isoforms in adult control (C) and 11A (Δ) mice (left panel): muscle (Mus), bone, skin, brain, lung, heart, adipose (Adip) and spleen (Spl). ΔFosB isoforms are expressed in osteoblasts derived from calvariae of control (C) and ΔFosB (Δ) animals (right panel).

Figure 2:
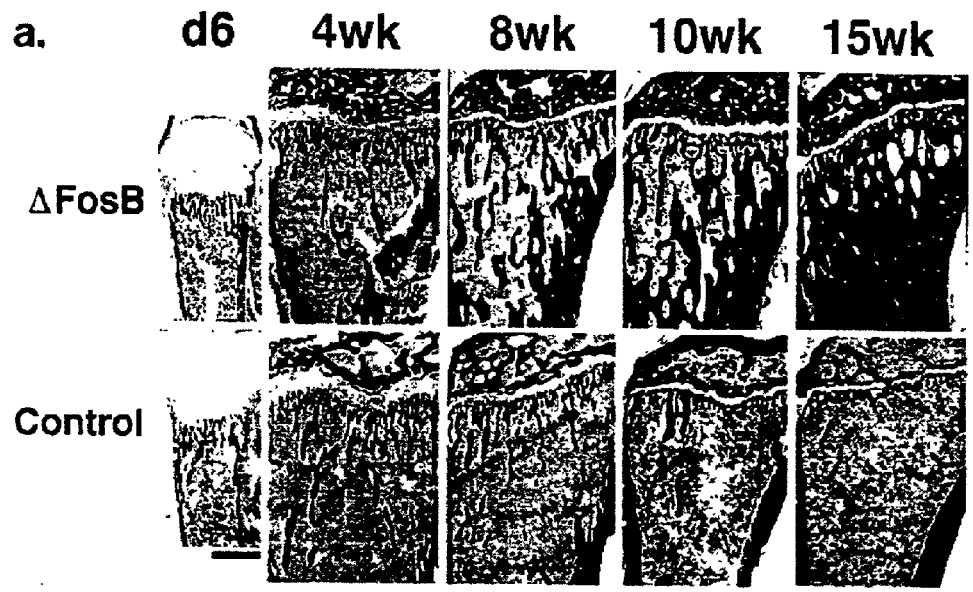
Figure 2:
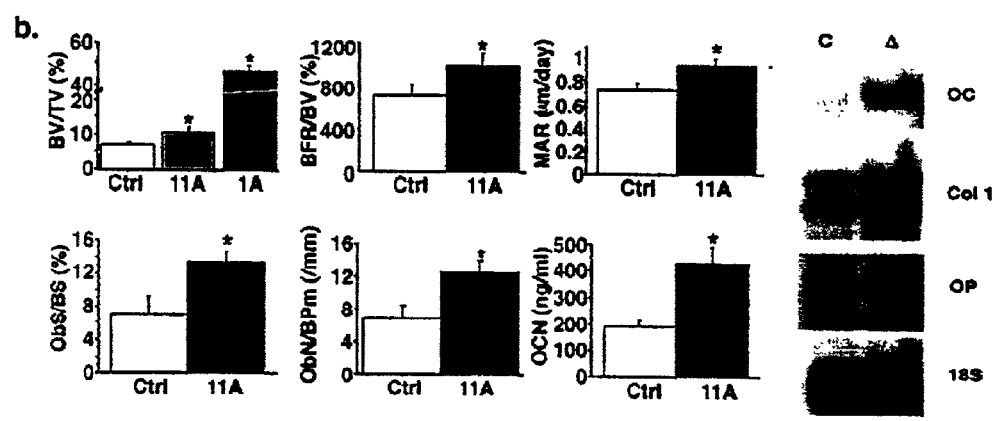
Figure 2:
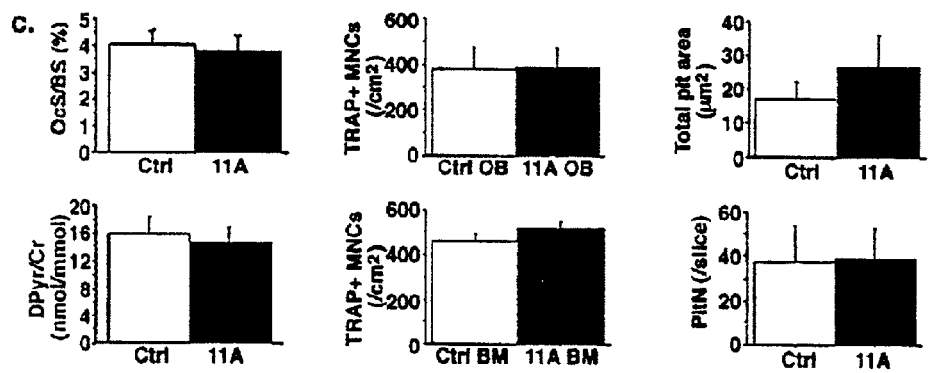

FIGS. 2 A–C. Progressive osteosclerosis in mice overexpressing ΔFosB.

A. Von Kossa-stained proximal tibiae from control (lower panel) and 1A ΔFosB (upper panel) mice at 6 days (d6), 4 weeks (4wk), 8 weeks (8wk), 10 weeks (10wk) and 15 weeks (15wk). B. Bone formation: Increased trabecular bone volume (BV/TV), bone formation rate (BFR/BV), mineral appositional rate (MAR), osteoblast surface (ObS/BS), osteoblast number (ObN/BPm) and serum osteocalcin (OCN) in ΔFosB expressing mice (11A and 1A) and controls (Ctrl) at 10 weeks of age. Northern blot analysis, of total RNA from calvariae of control (C) and 11A ΔFosB (Δ) mice at 2 days postnatally, demonstrating higher osteocalcin (OC), type I collagen (Col I) and osteoporntin (OP) mRNA expression in ΔFosB mice. C. Bone resorption: Unchanged osteoclast surface (OcS/BS), and urinary deoxypyrodinoline crosslinks (DPyr/Cr) in 10 week old control (Ctrl) and ΔFosB (11A) mice. Number of tartrate resistant acid phosphataste, stained multinuclear cells (TRAP+MNCs) detected in in vitro osteoclastogenesis analysis of primary osteoblasts (OB) and bone marrow cells (BM) from control (Ctrl) and ΔFosB (11A) mice. Bone resorption of authentic osteoclasts from control (Ctrl) and ΔFosB (11A) mice on dentin slices.

Figure 3:
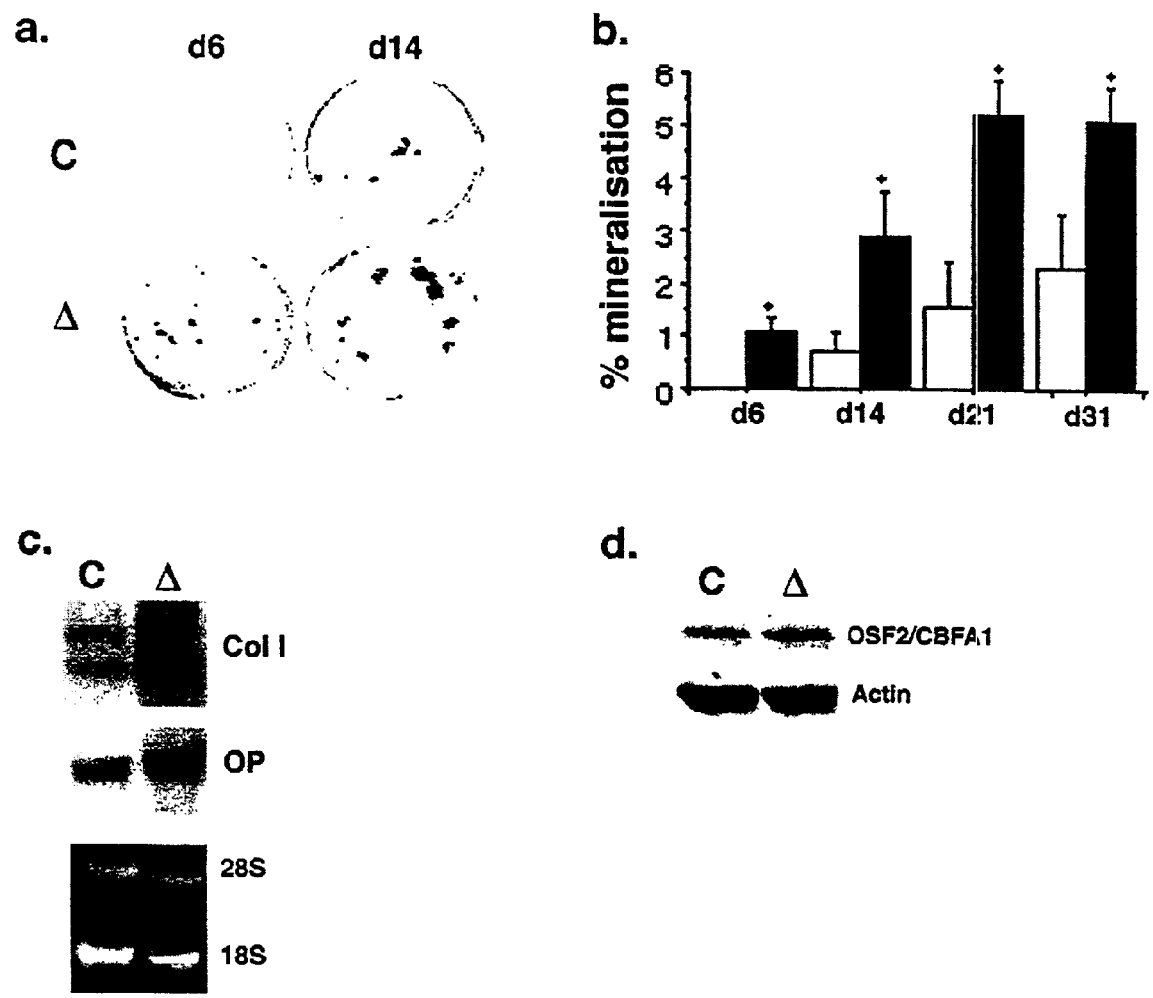

FIGS. 3 A–D. Cell-autonomous increased osteoblastogenesis in primary calvarial cultures of ΔFosB mice.

A. Extracellular matrix mineralization in control (C) and ΔFosB (Δ) calvarial cultures at days 6 (d6) and 14 (d14), Von Kossa staining. B. Quantitation of mineralization in control (open bars) and ΔFosB (shaded bars) cultures at days 6 (d6), 14 (d14), 21 (d21) and 31 (d31). C. Northern blot analysis of total RNA of control (C) and ΔFosB (Δ) primary osteoblast cultures at confluency (d0). Col I: type I collagen, OP: osteopontin. Equal loading was verified by ethidium bromide staining. D. Western blot analysis of whole cell extracts from control (C) and ΔFosB (Δ) primary osteoblast cultures at confluency (d0). Equal protein loading was demonstrated by reprobing with an anti-actin antibody.

Figure 4:
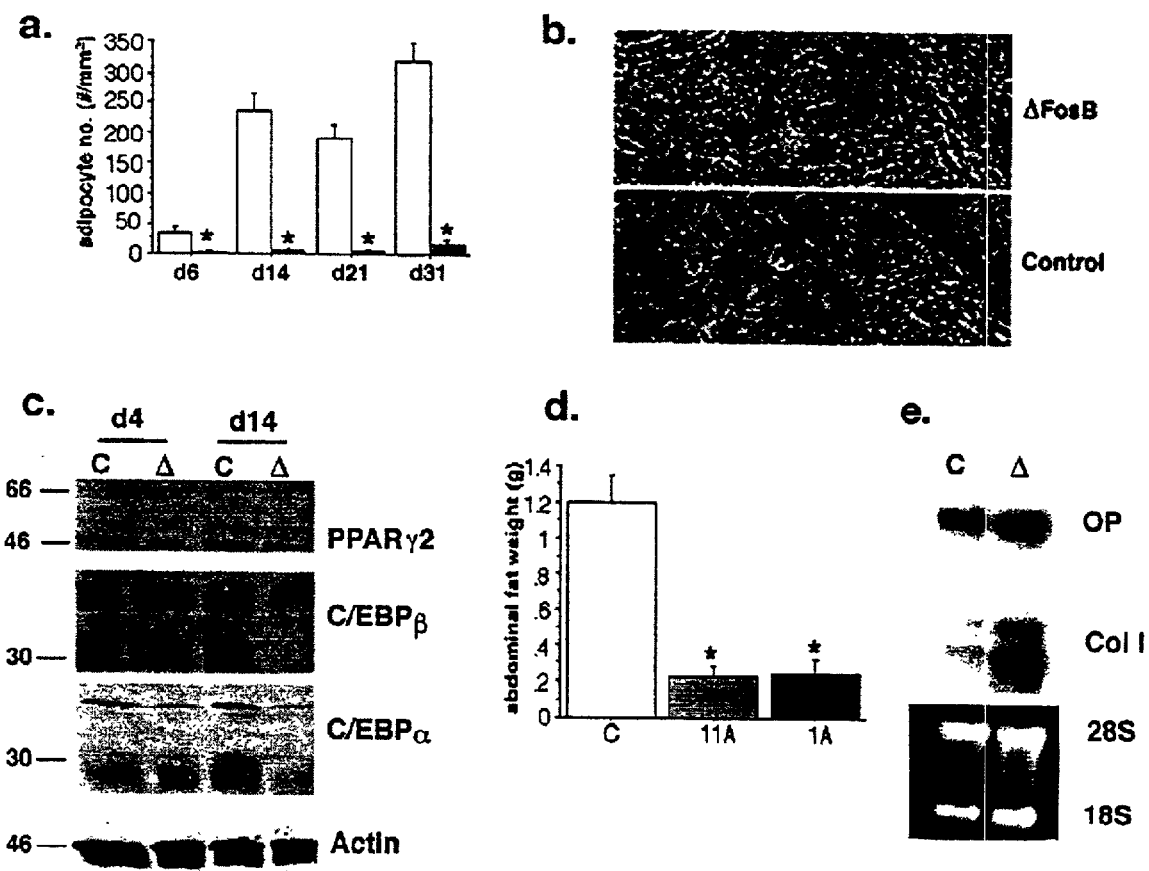

FIGS. 4 A–E. Decreased adipogenesis in primary calvarial and bone marrow stromal cell cultures of ΔFosB mice.

A. Adipocyte numbers in control (open bars) and ΔFosB (shaded bars) osteoblast cultures. B. Alkaline phosphatase/Oil Red O-staining of primary ΔFosB (top panel) and control (bottom panel) calvarial cultures at day 14 of mineralization. C. Western blot analysis of whole cell extracts from primary control (C) and ΔFosB (Δ) calvarial cultures at days 4 (d4) and 14 (d14) of mineralization. D. Abdominal fat weight in 10 week old control (C) and ΔFosB (1A and 11A) mice. E. Northern blot analysis of total RNA from primary control (C) and ΔFosB (Δ) bone marrow stromal cell cultures, treated with adipogenic agents as described in Methods, OP: osteopontin, Col I: type I collagen. Equal loading was verified by ethidium bromide staining.

Figure 5:
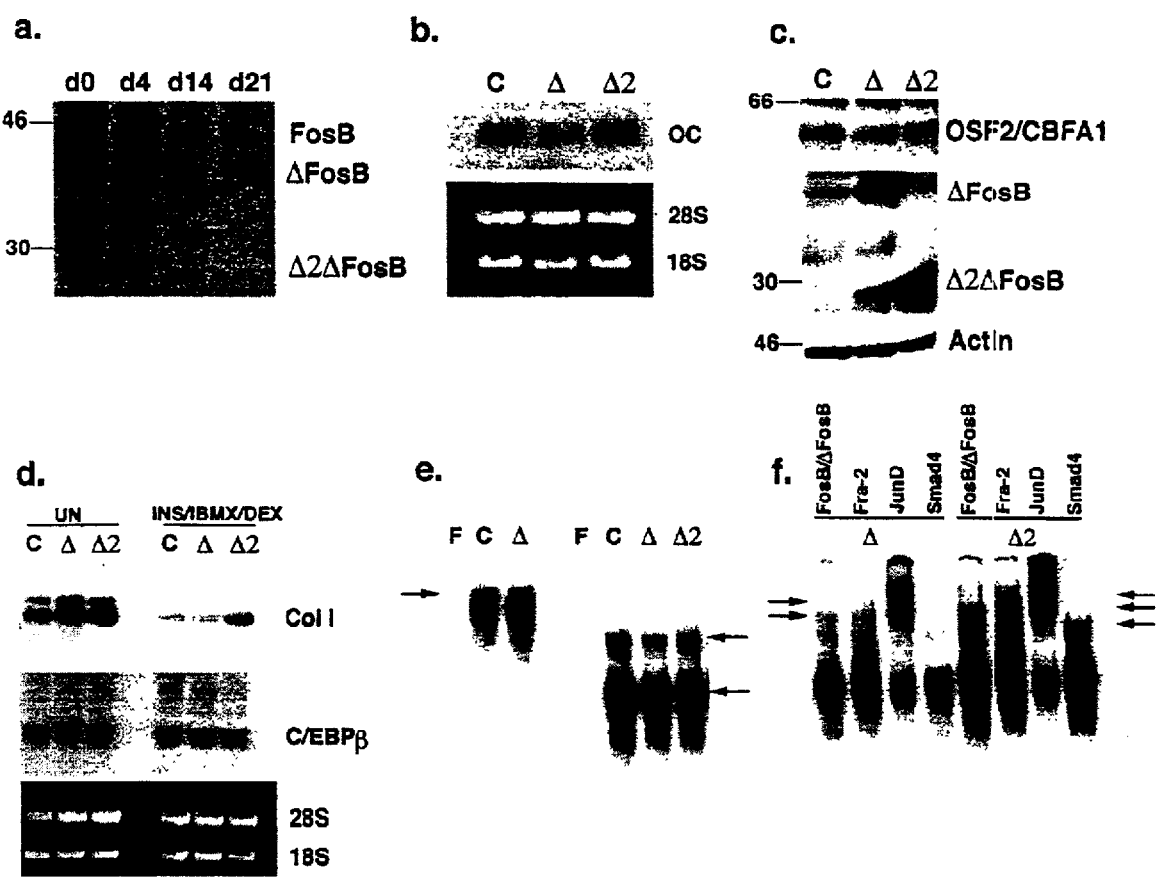

FIGS. 5 A–F. Molecular in vitro analysis of the role of ΔFosB isoforms during osteoblast differentiation.

A. Nuclear extracts of primary confluent (d0) and mineralizing cultures from calvariae of CD1 mice at days 4 (D4), 14 (D14) and 21 (D21) were analyzed for the expression of FosB and ΔFosB isoforms by Western blot. B. Northern blot analysis of total RNA from C2C12 cells stably transfected with empty vector (C), ΔFosB (Δ) and Δ2ΔFosB (Δ2) isoforms. Cells were treated with 300 ng/ml rhBMP-2 for 48 hrs prior to harvesting for RNA extraction. OC: osteocalcin. Equal loading is demonstrated by ethidium bromide staining. C. Western blot analysis of nuclear extracts following transient transfection of primary osteoblasts derived from CD1 calvariae with empty vector (C), ΔFosB (Δ) or Δ2ΔFosB (Δ2). D. Northern blot analysis of total RNA from 3T3-L1 pre-adipocytes, stably transfected with empty vector (C), ΔFosB (Δ) and Δ2ΔFosB (Δ2). Cells were either untreated (UN) or stimulated with insulin, isobutylmethylxanthine and dexamethasone (INS/IBMX/DEX) for 48 hours prior to RNA extraction. Equal loading was verified by ethidium bromide staining. E. Nuclear extracts from primary osteoblast cultures of control (C) and ΔFosB mice (left panel) and from the C2C12 stable cell lines expressing empty vector (C), ΔFosB (Δ), and Δ2ΔFosB Δ2) [right panel] were analyzed by EMSA using a consensus AP-1 oligonucleotide probe. Complexes formed are indicated by arrows. F: reaction mixture containing radiolabelled AP-1 probe without nuclear extracts. F. Antibody-supershift analysis of the complexes formed on a consensus AP-1 oligonucleotide probe using extracts from the C2C12 stable cell lines overexpressing the ΔFosB (Δ) and Δ2ΔFosB (Δ2) isoforms. Antibodies used are indicated; supershifted complexes are depicted by arrows.

DETAILED DESCRIPTION OF THE INVENTION

A. General Description

The present invention is based on the finding that overexpression of ΔFosB in mice, using a tetracycline-regulated system, resulted in increased bone formation throughout the skeleton and profound osteosclerosis. This phenotype is cell-autonomous in osteoblasts. In addition, ΔFosB inhibits adipogenesis both in vivo and in vitro, and downregulates the expression of early markers of adipocyte differentiation.

The present invention provides methods of identifying agents that modulate osteogenesis and adipogenesis by monitoring the expression of ΔFosB. The present invention also contemplates the use of the identified agents to treat specific diseases associated osteogenesis or adipogenesis. Moreover, the present invention provides methods of identifying genes that are modulated by ΔFosB or modulates ΔFosB. These genes are useful as tools for diagnosing and treating diseases, and as targets for identifying potential drugs for treating diseases.

B. Specific Embodiments

1. ΔFosB

ΔFosB is derived from the fosB gene via alternative splicing. As used herein the term "ΔFosB" refers to a protein described by Nakabeppu et al. (1991, which is incorporated herein by reference in its entirety). The term also encompasses naturally occurring ΔFosB from various animal species and allelic variants that have a slightly different amino acid sequence than the protein described by Nakabeppu et al. (1991). Contemplated ΔFosB from other species include but are not limited to human, rabbit, rat, murine, porcine, bovine, ovine, equine, and non-human primate species. Allelic variants, though possessing a slightly different amino acid sequence, will still have the ability to modulate bone formation.

Moreover, the term includes conservative variants of ΔFosB described by Nakabeppu et al. (1991). Conservative variant refers to alterations in the amino acid sequence of ΔFosB that do not alter the functional activity of ΔFosB such as modulating bone formation. The amino acid sequence of ΔFosB can be altered, for example to render ΔFosB more hydrophilic or hydrophobic without adversely affecting the activity of ΔFosB.

Such conservative mutations include but are not limited to mutations that switch one amino acid for another within one of the following groups:

1. Small aliphatic, nonpolar or slightly polar residues: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic, nonpolar residues: Met, Leu, Ile, Val and Cys; and
5. Aromatic residues: Phe, Tyr and Trp.

The types of substitutions selected may be based on the analysis of the frequencies of amino acid substitutions between homologous proteins of different species developed by Schulz et al., Principles of Protein Structure, Springer-Verlag, 1978, pp. 14–16, on the analyses of structure-forming potentials developed by Chou and Fasman, Biochemistry 13, 211, 1974 or other such methods reviewed by Schulz et al., Principles in Protein Structure, Springer-Verlag, 1978, pp. 108–130, and on the analysis of hydrophobicity patterns in proteins developed by Kyte and Doolittle, J. Mol. Biol. 157: 105–132, 1982.

The term "ΔFosB" also includes peptides that retain the functional activity of ΔFosB such as modulating bone formation. The peptides can be any length of at least 5, 8, 10, 15, 20 or more amino acids. It is also pointed out that these peptides are useful as antigens for generating antibodies.

Further, the term encompasses protein isolated from a natural source. A protein is said to be isolated when physical, mechanical, or chemical methods are employed to remove the protein from cellular constituents that are normally associated with the protein. A skilled artisan can readily employ standard purification methods to obtain an isolated ΔFosB protein. The term also encompasses ΔFosB protein obtained by recombinant means or chemical means.

As used herein, the term "nucleic acid encoding ΔFosB" encompasses deoxyribonucleic acids (DNAs) and ribonucleic acids (RNAs) including but not limited to genomic DNA, cDNA, mRNA, and antisense molecules. The nucleic acid molecules of the present invention also include native or synthetic, RNA, DNA, or cDNA, that encode ΔFosB. The term includes nucleic acids encoding all of the ΔFosB proteins encompassed by the term "ΔFosB" discussed above, including but not limited to, variants, allelic variants, and naturally occurring ΔFosB from various animal species.

2. Transgenic Animals

As used herein, the term "transgenic animal" refers to any animal, preferably a non-human animal, whose genome has been altered by the introduction of a transgene. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse.

As used herein, the term "transgene" refers to a nucleic acid sequence (encoding, e.g., a IL-6 polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

The procedure for producing a transgenic animal is known in the art (Hogan et al., (1986) "Manipulating the Mouse Embryo: A Laboratory Manual", Cold Spring Harbor Laboratory, Cold Spring Harbor, N.Y., USA; and U.S. Pat. No. 4,873,191). Generally, the transgene is introduced into the cell, directly or indirectly by introduction into a precursor of the cell, by way of deliberate genetic manipulation, such as by microinjection or by infection with a recombinant virus. The term genetic manipulation refers to the introduction of a recombinant DNA molecule. This molecule may be integrated within a chromosome, or it may be extrachromosomally replicating DNA. The transgene encoding a desired polypeptide, for example ΔFosB, is linked to one or more regulatory regions. Selection of the appropriate regulatory region or regions is a routine matter, within the level of ordinary skill in the art. The regulatory regions may comprise a promoter region for functional transcription, as well as a region situated 3' of the gene of interest, and which specifies a signal for termination of transcription and a polyadenylation site. It may also include an enhancer region.

Promoters that may be used in the present invention include both constitutive promoters and regulated (inducible) promoters. The promoter may be naturally responsible for the expression of the nucleic acid. It may also be from a heterologous source. In particular, it may be promoter sequences of eukaryotic or viral genes. For example, it may be promoter sequences derived from the genome of the cell which it is desired to infect. Likewise, it may be promoter sequences derived from the genome of a virus, including the adenovirus used. In this regard, the promoters include but are not limited to E1A, MLP, HCMV and RSV genes and the like. In addition, the promoter may be modified by addition of activating or regulatory sequences or sequences allowing a tissue-specific or predominant expression.

To control the expression of a transgene product, the transgene is linked to an inducible promoter. Inducible promoters include any promoter capable of increasing the amount of gene product produced, by a given gene, in response to exposure to an inducer. Inducible promoters are known to those familiar with the art and a variety exist that could conceivably be used to drive expression of the transgene. Examples of some inducible promoters include mouse mammary tumor virus (MMTV) steroid-inducible promoter, heat shock promoter, HLA-DR promoter, steroid hormone receptor (Cicatiello et al., 1995, Mol Endocrinol, 9: 1077–1090), retinoic acid receptor (Mendelsohn et al., 1994, Dev (1994) 45(3): 227–241), tetracycline-regulated transcriptional modulators (Furth et al., 1994, Proc Natl Acad Sci., 91(20): 9302–9306.), cytomegalovirus (CMV) immediate-early; retroviral LTR (Choate et al., 1997 Hum Gene Ther., 8(8):895–901.), metallothionein-1 (Fattori et al., 1994, Blood 83:2570–2579). Tetracycline-regulated transcriptional modulators and CMV promoters are also described in WO 96/01313, and U.S. Pat. Nos. 5,168,062, and 5,385,839.

The most widely used method for the production of transgenic animals is the microinjection of DNA into the pronuclei of fertilized embryos. This method is efficient for the production of transgenic mice but is much less efficient for the production of transgenic animals using large mammals such as cows and sheep. For example, it has been reported that 1,000 to 2,000 bovine embryos at the pronuclear stage must be microinjected to produce a single transgenic cow at an estimate cost of more than $500,000 (Wall et al., (1992) J. Cell. Biochem. 49:113). Furthermore, microinjection of pronuclei is more difficult when embryos from domestic livestock (e.g., cattle, sheep, pigs) is employed as the pronuclei are often obscured by yolk material. While techniques for the visualization of the pronuclei are known (i.e., centrifugation of the embryo to sediment the yolk), the injection of pronuclei is an invasive technique which requires a high degree of operator skill.

Alternative methods for the production include the infection of embryos with retroviruses or with retroviral vectors. Infection of both pre-and post-implantation mouse embryos with either wild-type or recombinant retroviruses has been reported (Jaenisch (1976) Proc. Natl. Acad. Sci. USA, 73:1260–1264; Jaenisch et al. (1981) Cell 24:519; Stuhlmann et al., (1984) Proc. Natl. Acad. Sci. USA, 81:7151; Jahner et al., (1985) Proc. Natl. Acad Sci. USA, 82:6927–6931; Van der Putten et al., (1985) Proc. Natl. Acad Sci. USA, 82:6148–6152; Stewart, et al., (1987) EMBO J., 6:383–388). The resulting transgenic animals are typically mosaic for the transgene since incorporation occurs only in a subset of cells which form the transgenic animal. In addition to the production of mosaic founder animals, infection of embryos with retrovirus (which is typically performed using embryos at the 8 cell stage or later) often results in the production of founder animals containing multiple copies of the retroviral provirus at different positions in the genome which generally will segregate in the offspring. Infection of early mouse embryos by co-culturing early embryos with cells producing retroviruses requires enzymatic treatment to remove the zona pellucida (Hogan et al. (1994) in Manipulating the Mouse Embryo: A Laboratory Manual, 2nd Ed., Cold Spring Harbor Laboratory Press, Cold Spring Harbor, N.Y., pp. 251–252).

An alternative means for infecting embryos with retroviruses is the injection of virus or virus-producing cells into the blastocoele of mouse embryos (Jahner et al., 1982) Nature 298:623–628). As is the case for infection of eight cell stage embryos, most of the founders produced by injection into the blastocoele will be mosaic. The introduction of transgenes into the germline of mice has been reported using intrauterine retroviral infection of the midgestation mouse embryo (Jahner et al., 1982 supra).

In summary, a method for producing a transgenic animal, which can be stably bred to produce offspring containing the gene, comprises the following steps:
  (a) isolating a fertilized oocyte from a first female animal;
  (b) transferring the transgene into the fertilized oocyte;
  (c) transferring the fertilized oocyte containing the transgene to the uterus of the same species as the first animal;
  (d) maintaining the second female animal such that
    (i) the second female animal becomes pregnant with the embryo derived from the fertilized oocyte containing the transgene,
    (ii) the embryo develops into the transgenic animal, and
    (iii) the transgenic animal is viably born from the second female animal;
wherein the transgenic animal has the genetic sequence for the desired protein and is capable of being bred to produce offspring having cells stably containing the desired genetic sequence.

Chen et al. (1998) report the generation of several lines of transgenic mice that direct transgene expression to specific brain regions, including the striatum, cerebellum, CA1 region of the hippocampus, or deep layers of cerebral neocortex. These mice were generated using a modified tetracycline-regulated system under the control of the neuron-specific enolase promoter. Transgene expression in these mice can be turned off completely with low doses of doxycycline (a tetracycline derivative) and driven to very high levels in the absence of doxycycline. The methods for obtaining the transgenic mice are described by Chen et al. (1998).

3. Methods of Identifying Agents that Modulate Bone Formation and Adipogenesis

The present invention provides a method for identifying agents that modulate bone formation. The method comprising administering a test agent and monitoring the expression of ΔFosB to determine whether the agent modulates bone formation, wherein an increase or decrease in the expression of ΔFosB expression indicates that the agent modulates bone formation. Moreover, an increase in the expression ΔFosB indicates that the agent is an inducer or promoter of bone formation, while a decrease in expression of ΔFosB indicates that the agent is an inhibitor of bone formation.

The present invention also provides a method for identifying agents that modulate adipogenesis. The method comprising administering a test agent and monitoring the expression of ΔFosB to determine whether the agent modulates adipogenesis or adipocyte differentiation, wherein an increase or decrease in the expression of ΔFosB expression indicates that the agent modulates adipogenesis. Moreover, an increase in expression ΔFosB indicates that the agent is an inhibitor of adipogenesis, while a decrease in expression of ΔFosB indicates that the agent is an inducer or promoter of adipogenesis.

As used herein, the term "agent" or "test agent" refers to any compound or molecule that is to be tested.

As used herein, the term "modulator" refers to any agent that alters; the expression of a specific activity, such as bone formation, adipogenesis or ΔFosB expression. As used herein, the term "modulate" or "modulates" means alters or changes. Thus, a test agent that modulates the expression of bone formation alters or changes bone formation, and a modulator of bone formation increases or decreases bone formation.

As used herein, the term "inducer" or "promoter" refers to any agent that induces, enhances, promotes or increases a specific activity, such as bone formation, adipogenesis, or ΔFosB expression.

As used herein the term "inhibitor" or "repressor" refers to any agent that inhibits, suppresses, represses, or decreases a specific activity, such as bone formation, adipogenesis, or ΔFosB expression.

Examples of agents of the present invention include but are not limited to peptides, small molecules, and antibodies. Agents can be randomly selected or rationally selected or designed. As used herein, an agent is said to be "randomly selected" when the agent is chosen randomly without considering the specific interaction between the agent and the target compound or site. As used herein, an agent is said to be "rationally selected or designed", when the agent is chosen on a nonrandom basis which takes into account the specific interaction between the agent and the target compound or site and/or the conformation in connection with the agent's action.

It is known that isoforms of ΔFosB are induced after many types of chronic perturbation such as exposure to cocaine, amphetamine, nicotine, opiates, antidepressants, and antipsychotics. Nestler et al. (1999) report that once induced ΔFosB isoforms persists in the brain for relatively long periods due to their extraordinary stability. Accordingly, agents that are rationally selected to modulate osteogenesis and adipogenesis include but are not limited to drugs of abuse, antidepressants, and antipsychotics. Specific examples of drugs of abuse include but are not limited to cocaine, amphetamine, nicotine, and opiate derivatives.

The methods of the present invention may be performed using in vitro cells (cultured cells) and cell lysates, specifically nuclear extracts. Examples of cells contemplated for identifying agents that modulate bone formation include but are not limited to calvarial cells, osteoblasts, osteoclasts, chondrocytes, and pluripotent precursor cells, such as multipotent bone marrow stromal cells. Specific examples of osteoblast cell lines include MC3T3-E1, C2C12, MG-63 cells, U2OS cells, UMR106 cells. ROS 17/2.8 cells, SaOS2 cells, and the like are provided in the catalog from the ATCC. Additionally, bone and cartilage cell lines established from transgenic mice may be used. Examples of cells that are useful for identifying agents that modulate adipogenesis include but are not limited to adipocytes, preadipocytes, and pluripotent precursor cells, such as multipotent bone marrow stromal cells. Specific example of adipocyte cell lines include 3T3-L1 preadipocytes, 3T3 F422A, and ob 1771. Cell lysates and nuclear extracts may be obtained from the contemplated cells by methods routinely practiced (Schreiber et al., 1989).

Further, U.S. Pat. No. 6,082,364 discloses pluripotent stem-like D1 cells, obtained from bone marrow, capable of differentiating into osteocytes, chondrocytes and adipocytes, depending on the environment encountered and treatment used. If systemically administered, the cells migrate to bone marrow. The cells may be transformed with recombinant DNA for the expression of both reporter genes and biological factors, such as growth factors. The patent teaches systemic administration of the cells to treat osteoporosis, osteolysis, and to improve bone implant adherence, augment bone growth or bone repair, augment cartilage repair, augment fat production for, e.g., breast augmentation.

The methods of the present invention may also be performed using, whole animals, preferably non-human transgenic animals. Preferred non-human transgenic animals include those that overexpress ΔFosB. Specific examples of such transgenic animals include animals carrying the TetOP-ΔFosB gene and bigenic NSE-tTA×TetOp-ΔFosB animals (Chen et al., 1998). Most preferably, these animals are transgenic mice. In another embodiment, cells obtained from transgenic animals are used as the source of ΔFosB for identifying agents that modulate osteogenesis or adipogenesis.

Methods for determining whether a test agent alters the expression of ΔFosB include performing analyses and assays well known to the skilled artisan. Examples include but are not limited to histochemical analyses, osteoclast like cell (OCL) formation assay, authentic osteoclast pit formation assay, Northern blot analysis, Western blot analysis, and electrophoretic mobility shift assays (EMSA) and supershift analysis. Other methods contemplated by the present invention for identifying test agents that modulate ΔFosB expression include PCR analyses, two hybrid screening assays (Fields et al., (1989) Nature 340:245; Gyuris et al., (1993) Cell, 75:791; Harper et al., (1993) Cell 75:805; Serrano et al., (1993) Nature 366:704; Hannon et al., (1993) Genes & Dev. 7:2378) and reporter gene systems. In certain embodiments, the reporter gene can encode beta-galactosidase. In other embodiments, the reporter gene can encode chloramphenicol acetyltransferase (CAT), luciferase, and other reporter genes. For example, the reporter gene could be under the control of a promoter that ΔFosB interacts with. Thus, the expression of the reporter indicates the expression of ΔFosB.

Transgenic animals administered with the test agent can be sacrificed, and assays performed using specimens from the animals. Additionally, bone histomorphometric measurements (Parfitt et al., 1987), serum osteocalcin measurements, urinary creatine measurements, serum leptin measurements, and marrow smears can be performed to determine whether the test agent alters the expression of ΔFosB.

It is within the skill of the artisan to perform side-by-side control experiments for determining whether a test agent modulates ΔFosB expression. An increase in ΔFosB expression as compared to the control indicates that the test agent is a potential promoter of bone formation, while a decrease in ΔFosB expression as compared to the control indicates that the test agent is a potential inhibitor of bone formation. Likewise, an increase in ΔFosB expression as compared to the control indicates that the test agent is a potential inhibitor of adipogenesis, while a decrease in ΔFosB expression as compared to the control indicates that the test agent is a potential inducer of adipogenesis.

The methods of the present invention may also be performed using a cell free system.

The methods of the present invention may be modified or performed in any available format, including high throughput assays. High throughput assays are useful for screening a large number of compounds in a given period of time. In one embodiment, assays can be formed using nucleic acids, wherein nucleic acids are placed on a DNA chip. In another embodiment, assays using cell-based screening are performed. U.S. Pat. No. 6,103,479 discloses miniature cell array methods and apparatus for cell-based screening. Methods have been described for making uniform micro-patterned arrays of cells for other applications, for example photochemical resist-photolithograpy (Mrksich and Whitesides, Ann. Rev. Biophys. Biomol. Struct. 25:55–78, 1996). U.S. Pat. No. 6,096,509 provides an apparatus and method for real-time measurement of a cellular response of a test compound on a flowing suspension of cells, in which a homogeneous suspension of each member of a series of cell types is combined with a concentration of a test compound, directed through a detection zone, and a cellular response of the living cells is measured in real time as the cells in the test mixture are flowing through the detection zone. The patent teaches the use of the apparatus in automated screening of libraries of compounds. The methods disclosed in the U.S. Patents can be modified to determine whether test agents modulate the expression of ΔFosB using cells such as adipocytes or osteoblasts.

4. Methods of Using the Agents that Modulate the Expression of ΔFosB

The present invention is based in part on the finding that overexpression of ΔFosB in transgenic mice leads to increased bone formation throughout the skeleton and a continuous post-developmental increase in bone mass. The present invention is also based in part on the discovery that expression of ΔFosB inhibits adipogenesis both in vitro and in vivo and downregulates the expression of early markers of adipocyte differentiation. Additionally, the present invention is based in part on the conclusion that ΔFosB transcriptionally regulates osteoblastogenesis, since osteoblasts and adipocytes are thought to share a common precursor.

Osteogenesis is expected to be promoted by stimulating growth, differentiation, or activation of osteoblasts, while adipogenesis is expected to be promoted by stimulating growth, differentiation, or activation of adipocytes. Accordingly, an agent that modulates the expression of ΔFosB is potentially useful for modulating osteogenesis, adipogenesis, osteoblast proliferation and differentiation, adipocyte proliferation or differentiation, stromal stem cell differentiation, and pluripotent precursor cell differentiation. Thus, an agent that modulates the expression of ΔFosB is potentially useful for treating diseases or conditions associated with osteogenesis and adipogenesis and for regulating the differentiation and proliferation of osteoblasts and adipocytes.

As used herein, the term "osteogenesis" refers to bone formation.

As used herein, the term "adipogenesis" refers to the production of fat, the deposition of fat, or to the conversion of carbohydrate or protein to fat. The term is synonymous with "lipogenesis".

As used herein, the term "osteoblastogenesis" is the formation of osteoblasts.

As used herein, the term "differentiate" refers to having a different character or function from the original type of tissues or cells. Thus, "differentiation" is the process or act of differentiating.

As used herein, the term "proliferation" refers to the growth and production of similar cells.

As used herein, the term "treatment" refers to both therapeutic treatment and prophylactic, or preventative measures. The object of a treatment is to prevent or slow down (lessen) the disease or conditions and to ameliorate the symptoms.

In general, diseases and conditions associated with bone formation and metabolism include but are not limited to rickets, osteomalacia, osteopenia, osteosclerosis, renal osteodystrophy, osteoporosis (including senile and post-menopausal osteoporosis), Paget's disease, bone metastases, hypercalcaemia, hyperparathyroidism, osteopetrosis, periodontitis, and the abnormal changes in bone metabolism which may accompany rheumatoid arthritis and osteoarthritis. Some of these diseases are characterized by insufficient bone formation or bone loss, while others involve an abnormal thickening or hardening of bone tissue. Examples of diseases that would benefit from inhibiting abnormal thickening of the bone include osteopetrosis and osteosclerosis. A specific example is Pycnodysostosis (PYCNO) a rare, autosomal recessive trait characterized by osteosclerosis, short stature, acro-osteolysis of distal phalanges, bone fragility, clavicular dysplasia and skull deformities with delayed suture closure (Maroteaux et al., 1962, Presse Med. 70:999; Andren et al., 1962, Acta. Chir. Scand. 124:496). Therefore, agents identified as inhibitors of bone formation are potentially useful for treating PCYNO and other diseases or conditions characterized by osteosclerosis and osteopetrosis.

There are also many diseases and conditions characterized by the need to enhance bone formation. The most obvious is the case of bone fractures, where it would be desirable to stimulate bone growth and to hasten and complete bone repair. Agents that enhance bone formation are potentially useful in facial reconstruction procedures. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis.

In one embodiment of the invention, agents identified as inducers or stimulators of bone formation are potentially useful for repairing bone defects and deficiencies, for promoting bone healing in plastic surgery, stimulating bone ingrowth into non-cemented prosthetic joints and dental implants, elevating peak bone mass in pre-menopausal women, treating growth deficiencies, treating periodontal disease and defects, and other tooth repair processes, treating skeletal disorders, such as age-related osteoporosis, post-menopausal osteoporosis, glucocorticoid-induced osteoporosis or disuse osteoporosis and arthritis, or any condition that benefits from stimulation of bone formation. In an alternative embodiment of the invention, these agents by themselves or in combination with other agents are potentially useful in the repair of congenital, trauma-induced or surgical resection of bone (for instance, for cancer treatment), and in cosmetic surgery. In another embodiment of the invention, the agents identified by the method of the present invention and combinations thereof can be used for limiting or treating cartilage defects or disorders, and may be useful in wound healing or tissue repair.

Moreover, the agents identified as modulators of osteogenesis are potentially useful for enhancing or preventing the proliferation of osteoblasts, osteoclasts, and chondrocytes in vitro, depending on whether the agent is an inducer or an inhibitor of bone formation. These agents are also useful for inducing or inhibiting differentiation of pluripotent precursor cells, preferably bone marrow stromal stem cells, into osteoblasts. It is within the skill of the artisan to administer an agent to isolated cells in (culture and to observe differentiation or proliferation of the in vitro cells.

Generally, diseases associated with adipogenesis include body weight disorders such as obesity and cachexia, and nonshivering and shivering thermogenesis. Accordingly, in one aspect of the invention, the agents identified as modulators of adipogenesis are potentially useful for modulating body weight-related processes, including, for example, treatment of body weight disorders such as obesity and cachexia, and thermogenesis. Depending on the desired result, an agent identified to induce adipogenesis is potentially useful for increasing body weight and an agent identified to prevent adipogenesis is potentially useful for decreasing body weight.

Adipogenesis when it occurs in the bone marrow is deleterions because the bone becomes necrotic. Such bones are weak and prone to fracturing. However, adipogenesis in other locations of the body may be highly desirable, for example, in the breast for breast augmentation. Pluripotent bone marrow cells may be implanted directly into breast fat pouches. Agents that are identified as capable of inducing the differentiation of pluripotent bone marrow cells into adipocytes may be administered to increase the production of fat cells in the breast.

The agents identified as modulators of adipogenesis may also be used to induce or inhibit proliferation or differentiation of isolated preadipocytes or adipocytes in culture, for example 3T3-L1, 3T3 F422A, ob 1771, or preadipocytes and adipocytes from transgenic animals that can be induced to overexpress $\Delta$FosB. It is within the skill of the artisan to administer the test agent to the isolated preadipocytes or adipocytes and to observe the proliferation or differentiation of the in vitro cells.

5. Pharmaceutical Compositions and Methods of Delivery

The test agents and agents or compounds identified to be modulators of $\Delta$FosB expression can be administered to subjects either by themselves or in pharmaceutical compositions. As used herein, the term "pharmaceutical composition" refers to a composition comprising an agent together with a pharmaceutically acceptable carrier or diluent. As used herein, the term "carrier" in a composition refers to a diluent, adjuvant, excipient, or vehicle with which the agent or compound is mixed.

Pharmaceutical carriers are chosen such that side effects from the pharmaceutical compound are minimized and the performance of the agent is not canceled or inhibited to such an extent that the treatment or the function of the agent is ineffective. Carriers can also be used to facilitate administration of the compound, for example, to increase the solubility of the compound. A pharmaceutically acceptable carrier includes, but is not limited to, physiological saline, ringers, phosphate buffered saline, calcium carbonate, calcium phosphate, various sugars or types of starch, cellulose derivatives, gelatin, vegetable oils, and polyethylene glycols. Pharmaceutical compositions comprising test agents or agents identified by the present invention, can be in either solid or liquid form.

Solid form preparations of pharmaceutical compositions include powders, tablets, pills, capsules, cachets, suppositories, and dispersible granules. The term "preparation" is intended to include the formulation of the agent with encapsulating material as a carrier, providing a capsule in which the active component with or without other carriers, is surrounded by a carrier. Similarly, cachets and lozenges are included. Tablets, powders, capsules, pills, cachets, and lozenges can be used as solid dosage forms suitable for oral administration. A solid carrier can be one or more substances which may also act as diluents, flavoring agents, binders, preservatives, tablet disintegrating agents, or an encapsulating material. In powders, the carrier is a finely divided solid which is in a mixture with the finely divided active agent. In tablets, the active agent is mixed with the carrier having the necessary binding properties in suitable proportions and compacted in the shape and size desired. The powders and tablets preferably contain from five or ten to about seventy percent of the active agent or compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active agent, colorants, flavors, stabilizers, buffers, artificial and natural sweeteners, dispersants, thickeners, solubilizing agents, and the like.

The test agents and agents or compounds identified to modulate ΔFosB expression can be administered to the subject as pharmaceutically acceptable salts. Examples of pharmaceutically acceptable salts include acid addition salts such as those containing hydrochloride, sulfate, phosphate, sulfamate, acetate, citrate, lac ate, tartrate, methanesulfonate, ethanesulfonate, benzenesulfonate, p-toluenesulfonate, cyclohexylsulfamate and quinate. (See e.g., PCT/US92/03736). Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

The present invention provides methods of administering a test agent in the form of a pharmaceutical composition to subjects to determine whether the agent is effective in modulating ΔFosB expression, osteogenesis, or adipogenesis. Moreover, the present invention provides methods of administering a pharmaceutical composition comprising an agent identified to modulate ΔFosB expression to treat subjects diagnosed with diseases or conditions associated with osteogenesis or adipogenesis. In treating a patient exhibiting a disorder associated with osteogenesis or adipogenesis, a therapeutically effective amount of an agent or agents is administered. A therapeutically effective dose refers to that amount of the compound that results in amelioration of symptoms or a prolongation of survival in a patient. For example, an effective amount for therapeutic uses is the amount of the composition comprising an active agent that provides a clinically significant increase in healing rates in fracture repair; reversal of bone loss in osteoporosis; reversal of cartilage defects or disorders; prevention or delay of onset of osteoporosis; stimulation and/or inhibition of bone formation in fracture non-unions and distraction osteogenesis; increase and/or decrease in bone growth into prosthetic devices; repair of dental defects; increase or decrease in adipogenesis or obesity; and increase or decrease in loss of appetite. Such effective amounts will be determined using routine optimization techniques and are dependent on the particular condition to be treated, the condition of the patient, the route of administration, the formulation, and the judgment of the practitioner and other factors evident to those skilled in the art. The dosage required for the compounds of the invention (for example, in osteoporosis where an increase in bone formation is desired) is manifested as a statistically significant difference in bone mass between treatment and control groups. This difference in bone mass may be seen, for example, as a 5–20% or more increase in bone mass in the treatment group. Other measurements of clinically significant increases in healing may include, for example, tests for breaking strength and tension, breaking strength and torsion, 4-point bending, increased connectivity in bone biopsies and other biomechanical tests well known to those skilled in the art. General guidance for treatment regimens is obtained from experiments carried out in animal models of the disease of interest.

Depending on the specific conditions being treated, agents may be formulated and administered systemically or locally. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. Some methods of delivery that may be used include but are not limited to encapsulation in liposomes, transduction by retroviral vectors, localization to nuclear compartment utilizing nuclear targeting site found on most nuclear proteins, transfection of cells ex vivo with subsequent reimplantation or administration of the transfected cells, and a DNA transporter system.

Toxicity and therapeutic efficacy of agents or compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents or compounds which exhibit large therapeutic indices are preferred. The data obtained from cell culture assays and animal studies can be used in formulating a range of dosage for use in human. The dosage of such agents or compounds lies preferably within a range of circulating concentrations that include the $ED_{50}$ with little or no toxicity. The dosage may vary within this range depending upon the dosage form employed and the route of administration utilized.

For any agent used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC. The exact formulation, route of administration, and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

In general, the agents utilized in the pharmaceutical method of this invention can be administered to a typical human on a daily basis as an oral dose of about 0.1 mg/kg-1000 mg/kg, and more preferably from about 1 mg/kg to about 200 mg/kg. The parenteral dose will appropriately be about 20–100% of the oral dose. While oral administration may be preferable in most instances (for reasons of ease, patient acceptability, and the like), alternative methods of administration may be appropriate for selected compounds and selected defects or diseases. The dosages, however, may be varied depending upon the requirements of the patient, the severity of the condition being treated, and the agent being employed. As discussed above, determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Further, the agents or compounds for treating diseases and conditions identified by the present invention may also be co-administered with other well known therapeutic agents that are selected for their particular usefulness against the condition that is being treated. The agents can be combined with estrogens or estrogen-related compounds since estrogens are known to inhibit bone resorption. Typical estrogen compounds include estradiol, progesterone, and analogs thereof as are well known in the art. Other compounds include but are not limited to bisphosphonates and related compounds such as those set forth in U.S. Pat. No. 5,312,814, calcium supplements (Prince, R. L. et al., 1991, N. Engl. J. Med. 325:1189), vitamin D supplements (Chapuy M. C. et al., 1992, N. Engl. J. Med. 327:1637), sodium fluoride (Riggs, B. L. et al., 1992, N. Engl. J. Med. 327:620), androgen (Nagent de Deuxchaisnes, C., 1983, in Osteoporosis, a Multi-Disciplinary Problem, Royal Society of Medicine International Congress and Symposium Series No. 55, Academic Press, London, p. 291), and calcitonin (Christiansen, C., 1992, Bone 13 (Suppl. 1):S35).

Additionally, the agents or compounds identified in the present invention may also be co-administered with compounds effective for modulating obesity, anorexia, cachexia, and other diseases or conditions associated with excessive increase in weight or loss of appetite. U.S. Pat. No. 6,068,976, discloses a down regulator of ob gene, expression, BRL49653, which increases food intake and body weight in rats. The administration of an effective amount of an ob gene down regulator will be able to treat a patient suffering from anorexia, cachexia and other wasting diseases characterized by loss of appetite, diminished food intake or body weight loss. Additionally, it is known that glucocorticoids, have the properties of decreasing food consumption and body weight gain in rats. The administration of an effective amount of an ob gene up regulator will be able to treat a patient suffering from excessive food consumption and obesity, and related pathological conditions such as type II adult onset diabetes, infertility (Chehab, et al., Nature Genetics, 12:318–320, 1996), hypercholesterolemia, hyperlipidemia. cardiovascular diseases and hypertension. Thus, the present invention contemplates administering pharmaceutical compositions comprising agents identified as modulators of ΔFosB expression in combination with agents known to regulate weight and appetite for the treatment of diseases or conditions associated with excessive weight loss or gain and loss or increase in appetite.

The administration of these additional compounds may be simultaneous with the administration of the agents identified to be modulators of ΔFosB expression or may be administered in tandem with the administration of the compounds of the invention. Any suitable protocol may be devised whereby the various compounds to be included in the combination treatment are administered within minutes, hours, days, or weeks of each other. Repeated administration in a cyclic protocol is also envisioned.

6. Method of Identifying Genes Associated with ΔFosB Expression

The present invention also contemplates methods of identifying genes that are associated with ΔFosB expression, i.e., genes that may be regulated by ΔFosB expression or regulate ΔFosB expression. The present invention also contemplates identifying genes that are associated with osteogenesis and adipogenesis. Additionally, the present invention provides methods for the identification of compounds that modulate the expression of genes or the activity of gene products associated with abnormal bone formation or abnormal adipogenesis.

In higher organism, the expression of certain genes in a cell determines the life processes, e.g. development and differentiation, homeostasis, response to insults, cell cycle regulation, aging, apoptosis, etc., to be carried out by the cell. Alterations in gene expression changes the course of development of a normal cell. Clearly, which genes are expressed has a profound effect on the nature of any given cell. Accordingly, methods for analyzing gene expression are critical to basic molecular biological research. Identification of differentially-expressed genes can provide a key to diagnosis, prognosis, and treatment of a variety of diseases or condition states in animals, including humans, and plants. Additionally, these methods can be used to identify differentially-expressed sequences due to changes in gene expression level associated with predisposition to disease or conditions, preferably associated with osteogenesis or adipogenesis. Identification of such genes helps in development of new drugs and diagnostic methods for treating or preventing the occurrence of such diseases.

One way of analyzing gene expression in a particular cell is to perform differential gene expression assays, in which the expression of genes in different cells is compared and any discrepancies in expression are identified, where the presence of discrepancies indicates a difference in the classes of genes expressed in the cells being compared.

As used herein, the term "differential expression" refers to both quantitative as well as qualitative differences in the genes' temporal and/or tissue expression patterns. Thus, a differentially expressed gene may qualitatively have its expression activated or completely inactivated in normal versus abnormal bone formation state or abnormal body weight state, or under control versus experimental conditions. Such a qualitatively regulated gene will exhibit an expression pattern within a given tissue or cell type which is detectable in either control subject or subjects with a disorder, but is not detectable in both. Alternatively, such a qualitatively regulated gene will exhibit an expression pattern within a given tissue or cell type which is detectable in either control or experimental subjects, but is not detectable in both. As used herein, "detectable" refers to an RNA expression pattern which is detectable via the standard techniques of differential display, RT-PCR and/or Northern analyses, which are well known to those of skill in the art.

Models of normal and abnormal animals or cell lines can be used to identify differentially expressed genes that are modulated or regulated by ΔFosB. In one embodiment of the invention, transgenic animals, preferably mice, induced to overexpress ΔFosB and uninduced transgenic animals are used to study differential gene expression. In an alternative embodiment, cell lines derived from normal individuals and individuals with diseases including but not limited to osteoporosis, rickets, osteomalacia, osteopenia, osteosclerosis, renal osteodystrophy, Paget's disease, bone metastases, hypercalcaemia, hyperparathyroidism, osteopetrosis, periodontitis, obesity, anorexia, cachexia, and nonshivering and shivering thermogenesis, are utilized to study differential gene expression associated with ΔFosB expression.

In order to identify differentially expressed genes, RNA, either total or mRNA, may be isolated from the tissues of the animals or from the cells described above. RNA samples are obtained from tissues of experimental subjects and from corresponding tissues of control subjects. Any RNA isolation technique which does not select against the isolation of MRNA may be utilized for the purification of such RNA samples. See, for example, Ausubel, F. M. et al., eds., 1987–1993, Current Protocols in Molecular Biology, John Wiley & Sons, Inc. New York, which is incorporated herein by reference in its entirety. Additionally, large numbers of tissue samples may readily be processed using techniques well known to those of skill in the art, such as, for example, the single-step RNA isolation process of Chomczynski, P. (1989, U.S. Pat. No. 4,843,155), which is incorporated herein by reference in its entirety.

Transcripts within the collected RNA samples which represent RNA produced by differentially expressed genes may be identified by utilizing a variety of methods which are well known to those of skill in the art. For example, differential screening (Tedder et al., 1988, Proc. Natl. Acad. Sci. USA 85:208–212), subtractive hybridization (Hedrick et al., 1984, Nature 308:149–153; Lee et al., 1984, Proc. Natl. Acad. Sci. USA 88:2825), and, preferably, differential display (Liang, P. and Pardee, A. B., 1992, Science 257:967–971; U.S. Pat. No. 5,262,311, which is incorporated herein by reference in its entirety), may be utilized to identify nucleic acid sequences derived from genes that are differentially expressed.

U.S. Pat. No. 5,968,784 provides a method for tagging and identifying all of the expressed genes in a given cell population. This method thus allows even mRNAs with low copy number to be detected. By comparing gene expression profiles among cells, this method may be used to identify individual genes whose expression is associated with a pathological phenotype. Using high throughput DNA sequencing and associated information system support to analyze such DNA sequencing, the disclosed method also permits the generation of global gene expression profiles in a reasonable length and time. Thus, the patent provides a simple and rapid method of obtaining sufficient data to use in an information system known to those of skill in the art to obtain global gene expression profile and identify genes of interest.

Once potentially differentially expressed gene sequences have been identified via bulk techniques such as, for example, those described above, the differential expression of such putatively differentially expressed genes should be corroborated. Corroboration may be accomplished via, for example, such well known techniques as Northern analysis, quantitative RT PCR or RNase protection. Upon corroboration, the differentially expressed genes may be further characterized and identified.

7. Methods of Inhibiting ΔFosB Expression Using Nucleic Acids

The present invention also provides antisense nucleic acids and ribozymes which exhibit the ability to modulate osteogenesis and adipogenesis. Such molecules are designed to reduce or inhibit ΔFosB gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

As used herein, a sequence "complementary" to a portion of an RNA, refers to a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have also been shown to be effective at inhibiting translation of mRNAs as well (Wagner, R., 1994, Nature 372:333–335).

Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of target gene MRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The antisense oligonuculeotide may comprise a modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine.

The antisense oligonucleotide may also comprise at least one modified sugar moiety selected from the group including but not limited to arabinose, 2-fluoroarabinose, xylulose, and hexose. In yet another embodiment, the antisense oligonucleotide may comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Oligonucleotides of the invention may be synthesized by standard methods known in the art, e.g. by use of an automated DNA synthesizer (such as those that are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci.U.S.A. 85:7448–7451), etc.

A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue, in which case administration may be accomplished by another route (e.g., systemically).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences 8. Genetic Therapy As discussed above, the present invention provides methods of identifying genes associated with osteogenesis, adipogenesis, or ΔFosB expression, including genes that are regulated by ΔfosB expression and that regulates ΔfosB expression. The present invention also contemplates a method of delivering nucleic acid molecules, such as the ΔFosB nucleic acids, to target sites for the treatment of diseases associated with osteogenesis and adipogenesis.

Gene therapy is a method for delivering functionally active therapeutic or other forms of genes into targeted cells.

Initial efforts of gene transfer into somatic tissues have relied on indirect means called ex vivo gene therapy, wherein target cells are removed from the body, transfected or infected with vectors carrying recombinant genes, and re-implanted into the body. Techniques currently used to transfer DNA in vitro into cells include calcium phosphate-DNA precipitation, DEAE-Dextran transfection, electroporation, liposome mediated DNA transfer or transduction with recombinant viral vectors. These transfection protocols have been used to transfer DNA into different cell types including epithelial cells (U.S. Pat. No. 4,868,116), endothelial cells (WO89/05345), hepatocytes (Ledley et al., 1987 Proc Natl Acad Sci USA. 84(15):5335–9) fibroblasts (U.S. Pat. No. 4,963,489), lymphocytes (U.S. Pat. No. 5,399,346; ) and hematopoietic stem cells (U.S. Pat. No. 5,399,346).

Direct in vivo gene transfer has been carried out with formulations of DNA trapped in liposomes (Seol et al., 2000 In Vivo14(4):513–7, or in proteoliposomes that contain viral envelope receptor proteins (Gould-Fogerite et al., 1989, Gene 84(2):429–38), and with DNA coupled to a polylysine-glycoprotein carrier complex. In addition, "gene guns" have been used for gene delivery into cells (Australian Patent No. 9068389). Lastly, naked DNA, or DNA associated with liposomes, can be formulated in liquid carrier solutions for injection into interstitial spaces for transfer of DNA into cells (WO90/11092).

Viral vectors are often the most efficient gene therapy system, and recombinant replication-defective viral vectors have been used to transduce (i.e., infect) cells both ex vivo and in vivo. Such vectors include retroviral, adenovirus and adeno-associated and herpes viral vectors. Accordingly, in one embodiment the nucleic acids including genes, ribozymes, and antisense molecules associated with adipogenesis, osteogenesis, or ΔFosB expression can be subloned into an appropriate vector and transferred into a cell or tissue by gene transfer techniques discussed above.

In another embodiment, the nucleic acids associated with adipogenesis, osteogenesis, or ΔFosB expression can be provided to the cell or tissue using a transfection facilitating composition, such as cationic liposomes containing desired polynucleotides.

In light of the foregoing general discussion, the specific examples presented below are illustrative only and are not intended to limit the scope of the invention. Other generic and specific configurations will be apparent to those persons skilled in the art.

EXAMPLES

Materials and Methods

Histomorphometric and Biochemical Analyses: Ten week old 1A, 11A, and control mice were injected with calcein (20 mg/kg, Sigma MO) at 10 and 3 days before sacrifice, respectively, to label bone mineralization fronts. Mice were bred from heterozygous breeders, providing bitransgenic ΔFosB-expressing mice and monotransgenic non-expressing littermate controls. Specimens were fixed in 3.7% formaldehyde/PBS and embedded by standard procedures in methylmethacrylate resin. Five micromolar toluidine blue or 10 µm unstained sections were used for standard bone histomorphometric measurements (Parfitt et al., 1987) using the Osteomeasure system (OsteoMetrics, GA). Serum osteocalcin was measured by radioimmunoassay (Biomedical Technologies Inc, MA). Urinary deoxypyridinoline crosslinks were measured by the Pyrilinks-D assay (Metra Biosystems Inc, CA); urinary creatinine was measured enzymatically on a clinical chemistry analyser (BM/Hitachi 717, CA). Serum leptin was measured by a mouse specific immunoassay (Quantikine M, R&D Systems, Minneapolis). Marrow smears were carried out on humeri from control and 1A mice. The joints were removed and marrow was flushed out onto microscope slides using minimal essential medium Eagle, α-modification (α-MEM, Sigma), followed by Oil Red O and 1% toluidine blue staining. Adipocytes and total marrow cells were counted on five randomly selected fields of each smear from 4 mice of each genotype. Adipocyte number is expressed as a percentage of marrow cell number to allow for the reduction in bone marrow in the 1A mice. Data were analyzed by one-way ANOVA and Fisher's post-hoc test, with $p<0.05$ considered statistically significant.

Cell Culture and DNA Transfections: Primary murine calvarial cell cultures were prepared from 1–2 day old control or NSE-ΔFosB 11A mice and maintained as described by Bellows et al. (1990). Homozygous bitransgenic 11A litters were bred. The same breeder male and a non-transgenic female were used to provide monotransgenic non-expressing controls. At confluency, cultures were supplemented with 50 µg/ml ascorbic acid (Wako, Japan), 5 mM β-glycerophosphate (Sigma) and 10 nM dexamethasone (Sigma). Bone marrow cells were flushed from femora and tibiae of 4 week old mice and maintained in DMEM (Sigma) supplemented with 10% FBS and 1% penicillin/streptomycin. After 5 days in culture, plates were washed free of non-adherent cells and the adherent layer was cultured until confluent. Cells were detached and replated at a density of $2 \times 10^4/cm^2$. At confluency, cells were incubated with either osteoblastic or adipocytic-inducing agents as described (Quarles et al., 1992) before harvesting for experiments. The C2C12 myoblasts were maintained as described previously (Cao et al.). The osteoblastic phenotype was induced by incubating in DMEM, supplemented with 5% FBS and 300 ng/ml human recombinant BMP-2 for 48 hours. The MC3T3-E1 (pre-osteoblastic) and 3T3-L1 (pre-adipocytic) cell lines were purchased from ATCC and maintained according to standard protocols; the osteoblastic or adipocytic phenotype respectively was induced as described in Quarles et al. (1992) and Cao et al. (1991). Cells were transfected using lipofectamine (GIBCO BRL) according to the manufacturer's instructions. In transient expression studies, cells were harvested 48–72 hours post-transfection. To establish stable transfectants, cells were split 1:10, 72 hours post-transfection and selected in 0.5 mg/ml G418 (GIBCO) for 3–4 weeks.

Osteoclast Like Cell (OCL) Formation Assay: OCLs were generated as previously described by Aoki et al. (1993), then fixed and stained for tartrate-resistant acid phosphatase (TRAP; 34) and TRAP-positive multinucleated OCLs (nuclei>3) were counted.

Authentic Osteoclast Pit Formation Assay: In vitro bone resorption was assayed as described (Aoki et al., 1993). Resorption pits were measured using an Osteomeasure analysis system (Osteometrics,GA). Total pit area and number for each dentin slice were measured.

RNA Extraction and Northern Blot Analysis: Total RNA was extracted from cells with TRIZOL (GIBCO) according to manufacturer instructions. 20 µg total RNA were resolved in 1% denaturing agarose/formaldehyde gels and transferred onto Hybond-N nylon membranes (Amersham) as described (Sambrook et al., 1989). Membranes were sequentially hybridized with $^{32}$P-labelled cDNA probes for mouse osteocalcin, osteopontin, and collagen type 1. The C/EBP probe was obtained by RT-PCR using conditions described previously (Sabakatos et al., 1998).

Protein Extracts and Western Blot Analysis: Nuclear extracts from cells were prepared as described previously (Schreiber et al., 1989). Total cellular protein from tissues was prepared by sonication in modified RIPA buffer supplemented with proteinase and phosphatase inhibitors (REF). Protein concentration was determined by BCA assay (PIERCE, IL). Protein samples were analyzed by Western blot followed by chemiluminescent detection (Amersham, NJ) using standard techniques. All antibodies used were purchased from Santa Cruz Biotechnology (CA), except for OSF2/CBFA1.

Histochemical Analysis of Osteoblast Cultures: Calvarial osteoblast cultures were stained with alkaline phosphatase (Sigma) for osteoblasts and Oil Red O (Sigma) for adipocyte lipid. For measurement of adipocytes and mineralization, cultures were set up in 24 well plates and stained with Oil Red O and by a modified Von Kossa technique (Baron et al., 1983). The same wells were used to measure both percent mineralization and adipocyte number. Adipocytes were counted from 5 random fields of view under a light microscope at the 40× objective (0.1963 $mm^2$ view area). Mineralizing area was measured across the entire well. Three wells were measured at each time point in each of 2 experiments.

Electrophoretic Mobility Shift Assays (EMSA) and Supershift Analysis: EMSA was performed using a $^{32}$P-labelled double stranded oligonucleotide corresponding to the human collagenase TPA-response element, which contains an AP-1-binding site (GTCGACGTGAGTCAGCGCGC, SEQ ID NO: 1), as described (Sabakatos at., 1998). For supershift analysis, antibodies were incubated with nuclear extracts for 30 min on ice prior to addition of $^{32}$P-labelled oligonucleotide. Following electrophoresis, gels were dried and the complexes were visualized by autoradiography.

Figure 1:
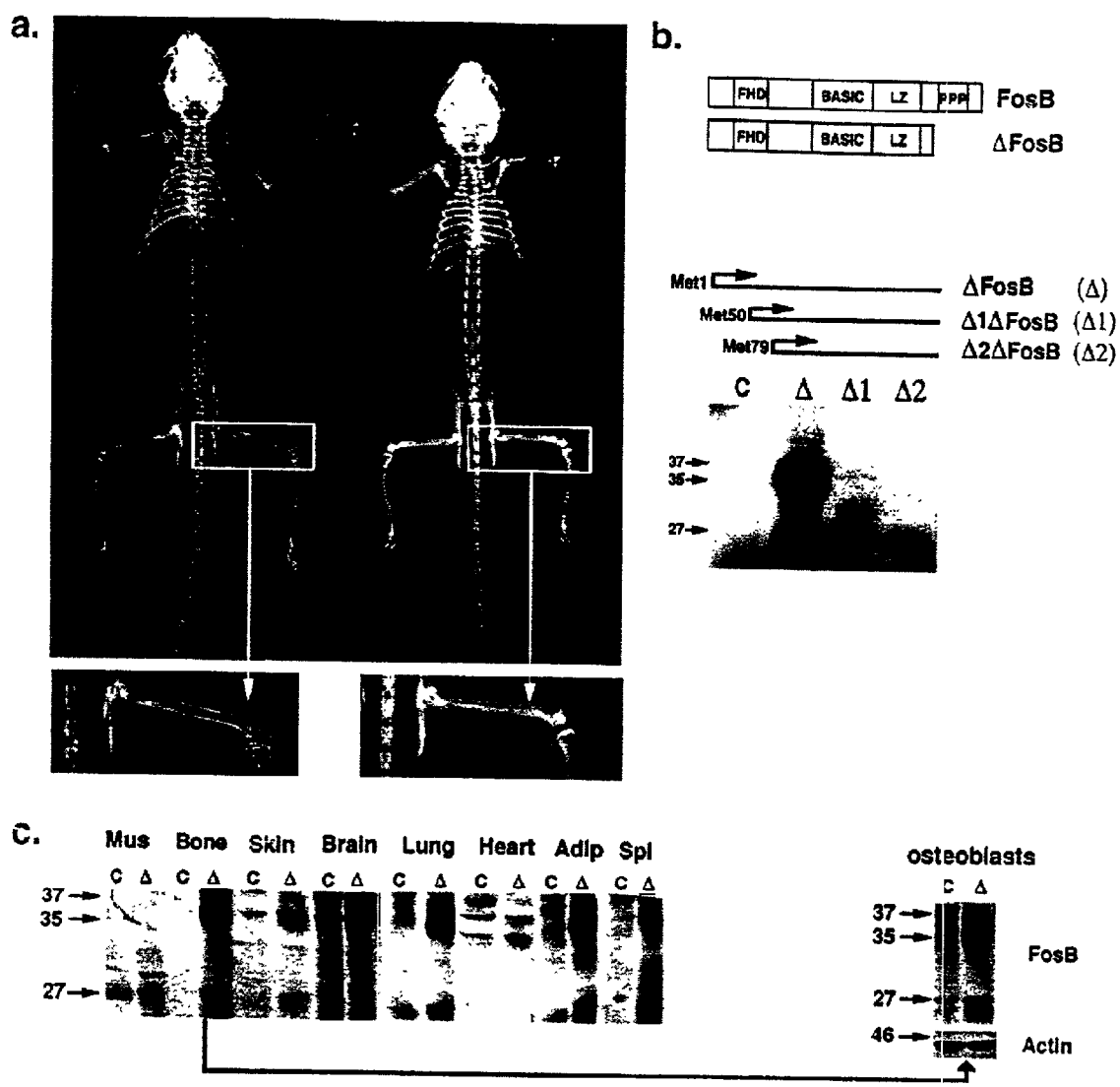
FIGS. 1 A–C. Increased bone density and tissue-specific expression of ΔFosB isoforms in the NSE-ΔFosB mice.

Example 1
NSE-FosB is Expressed in Transgenic Mice Exhibit Markedly Denser Bones The present invention is based in part on the finding that NSE-FosB expressed in transgenic mice exhibits denser bones. Although NSE-tTA (line A) x TetOp-ΔFosB (line 11) bitransgenic animals were initially generated to study the role of ΔFosB in the brain (Chen et al., 1998), showing inducible expression of ΔFosB in specific brain regions as well as altered behavioral responses (Kelz et al., 1999), it was observed that NSE (data not shown), and consequently ΔFosB (FIG. 1B), were expressed in osteoblasts, chondrocytes and adipocytes, when the animals were kept off doxycycline, but not in osteoclasts (data not shown). Transgenic mice kept off doxycycline from conception, leading to ΔFosB expression throughout development, were found to have strikingly increased bone density. This phenotype was even more dramatic in mice derived from another TetOp-ΔFosB founder line (line 1), which is known to express much higher levels of FosB (Chen et al., 1998). X-ray analysis of these NSE-ΔFosB founder lines showed that bone density was markedly increased throughout the skeleton in mature mice (FIG. 1A). As anticipated from the patterns of NSE expression, both lines expressed high levels of FosB isoforms (FIG. 1B) not only in brain, but also in bone (calvariae) and adipose tissue, and to a lesser extent in spleen and skin (FIG. 1C). Although significantly elevated in osteoblast preparations from the transgenic mice, ΔFosB isoforms were also expressed at detectable levels in wild-type osteoblasts (FIG. 1C).

NSE-ΔFosB mice were indistinguishable from control littermates at birth, but with advancing age trabecular bone volume increased markedly until the marrow space was almost entirely filled with lamellar bone (15 week-old 1A mice), (FIG. 2A) leading to extramedullary hematopoiesis and splenomegaly. The increased bone mass was proportional to gene dosage, since trabecular bone volume, although significantly increased in 11A mice, was much higher in 1A mice (FIG. 2B). Furthermore, the increased bone mass could be induced in mature animals by removing doxycycline or reversed by two weeks of doxycycline treatment (data not shown). These data exclude the possibility that the observed skeletal phenotype could be the consequence of developmental alterations. Calvarial bone thickness was also increased, indicating that bone derived from either intramembranous or endochondral ossification were equally affected. In contrast to c-Fos overexpressing mice (Grigoriadis et al., 1993, Wang et al., 1995), osteosarcoma was never observed. Osteoblasts were orderly, fluorochrome labels were sharp, and there was no marrow fibrosis or woven bone, indicating that bone formation, although markedly increased, is still a controlled process in these transgenic animals.

Example 2
Increased Bone Density in vivo is Due to Increased Bone Formation

The present invention is also based in part on the finding that increased bone density in vivo is due to increased bone formation. Possible pathways by which bone mass can increase in vivo all result from an imbalance between bone resorption and formation in favor of bone formation. Firstly, bone mass may be elevated due to impaired osteoclast function, resulting in an osteopetrosis characterized by the presence of many thin unremodelled trabeculae containing growth plate cartilage, and impaired tooth eruption (Soriano et al., 1991, Hayman et al., 1996, Seifert et al., 1985). A morphologically similar phenotype is observed when bone resorption is reduced due to impaired osteoclast differentiation (Johnson et al., 1992, Wang et al., 1992, Franzoso et al., 1997, Tondravi et al., 1997, Marks et al., 1976, Simonet et al., 1997). The third mechanism by which bone mass can increase in vivo is via increased bone formation (osteosclerosis). A phenotype as dramatic as the one reported here has however never been described. Only mild increases in bone density have been documented, following targeted disruption of the osteocalcin gene (Duey et al., 1996), after prolonged treatment with PTH or $PGE_2$ 17,18, or more recently in the leptin signaling-deficient ob/ob and db/db mice (Ducy et al., 2000).

Detailed static and dynamic histomorphometric analysis of proximal tibiae and biochemical analyses of 10-week old 11A mice demonstrated that the increased bone mass in NSE-ΔFosB mice results from increased bone formation rather than impaired bone resorption. Histomorphometric markers of osteoblast proliferation and function were increased, including serum osteocalcin levels, which reflects bone formation at the systemic level (FIG. 2B). In addition, the expression of genes encoding bone matrix proteins was also up-regulated in calvariae from NSE-ΔFosB mice (FIG. 2B). In contrast, neither osteoclast surface or number, nor urinary deoxypyrodinoline crosslinks were increased, demonstrating that bone resorption was not altered in vivo (FIG. 2C). In vitro bone resorption assays carried out on isolated NSE-FosB (11A) osteoclasts revealed no difference in pit number or size (FIG. 2C). Similarly, reciprocal co-culture experiments using osteoblasts and bone marrow from NSE-FosB (11A) or control animals, demonstrated no significant difference in osteoclastogenic potential of FosB marrow or osteoblasts (FIG. 2C). Tartrate-resistant acid phosphatase (TRAP) staining appeared normal in both neonate and mature mice. Finally, tooth eruption was neither impaired nor delayed, trabecular and cortical bone appeared normal at birth, and cartilage remnants were not detected within the secondary spongiosa, thereby further excluding osteopetrosis. Thus, the main cellular defect in these mice is a marked increase in bone formation, leading progressively to severe osteosclerosis.

Example 3
The Increase in Bone Formation is Cell-autonomous in the ΔFosB Transgenic Osteoblast Lineage The present invention is also based on the finding that bone formation is cell autonomous in ΔFosB transgenic osteoblast lineage. To determine whether the increased bone formation in NSE-ΔFosB mice was inherent to the osteoblast lineage or the result of systemic or microenvironmental changes, primary calvarial cultures were generated and differentiated in vitro. NSE-ΔFosB cultures demonstrated earlier and more rapid mineralized nodule formation, as well as increased expression of marker genes associated with the osteoblast phenotype, thus establishing a cell-autonomous effect of ΔFosB on osteoblasts and bone formation (FIGS. 3A–D).

Osteoblasts and adipocytes are believed to originate from a common mesenchymal precursor and are both found in long-term murine primary calvarial cultures (Bellows et al., 1994). A significant reduction in adipocyte number in calvarial cultures was observed from NSE-ΔFosB mice. The few adipocytes that differentiated in the NSE-ΔFosB cultures were less mature, with only few and small lipid droplets, in contrast to the large, numerous droplets observed in control calvarial cultures (FIGS. 4A,B). Consistently, expression of transcription factors associated with the adipocytic phenotype such as PPAR2, C/EBP and C/EBP was also decreased relative to wild-type cultures at all time points studied (FIG. 4C).

Confirming changes observed in vitro, abdominal fat levels were decreased in NSE-ΔFosB mice (FIG. 4D) and marrow smears demonstrated reduced adipocyte numbers (mean adipocytes/marrow cells (%)±SEM: control, 14.2±2; 11A, 2.3±1, p<0.05). Moreover, in vitro cultures of bone marrow stromal cells from ΔFosB mice treated with either osteogenic or adipogenic agents revealed a significant decrease in adipose cell number and maturation, as opposed to increased expression of genes associated with the osteoblast phenotype (FIG. 4E and data not shown). Thus, in vivo and in vitro results strongly suggest that ΔFosB overexpression favors commitment of early mesenchymal precursors to the osteoblast lineage, while repressing the differentiation of adipocytes.

The next and most important question was whether expression of ΔFosB isoforms is biologically significant or whether the observed phenotype merely results from overexpression of a protein that is normally not present in osteoblasts. Using an antibody that recognizes a common epitope in the FosB and ΔFosB isoforms, we found that while FosB levels remained unchanged, ΔFosB levels increased as the cultures differentiated, whereas expression of the further truncated Δ2ΔFosB isoform decreased in the same time frame (FIG. 5A). Thus, stage-specific alternative splicing of fosB mRNA and selective initiation site usage of FosB (Chen et al., 1997), rather than expression of FosB itself, regulates osteoblast differentiation.

Example 4
Repression of Adipocyte Differentiation In Vitro and In Vivo

Further, the present invention is based on the discovery that ΔFosB overexpression represses adipocyte differentiation. The mechanism by which FosB overexpression might induce differentiation of pluripotent precursor cells toward an osteoblast phenotype at the expense of the adipocytic pathway was then investigated. Using a combination of Northern and Western blot analysis following transient or stable overexpression of ΔFosB or the N-terminally truncated Δ2ΔFosB isoform in primary osteoblasts, or the MC3T3-E1 or C2C12 cell lines, we found that expression of bone matrix proteins and the osteoblast-specific factor OSF2/CBFA1 was upregulated specifically in cells expressing Δ2ΔfosB. Although the Δ2ΔFosB isoform should also be expressed in cells transfected with the full length ΔFosB, usage of the third methionine was not efficient in ΔFosB overexpressing cells, leading to low Δ2ΔFosB expression levels and, interestingly, a parallel decrease or lack of stimulation of osteoblast marker genes (FIGS. 5B, C and data not shown) further suggesting that Δ2ΔFosB may be involved in the transgenic phenotype. Surprisingly, expression of Δ2ΔFosB in 3T3-L1 preadipocytes not only down-regulated C/EBP mRNA expression even after treatment with adipogenic agents, but caused instead an increase in type I collagen mRNA levels (Dorheim et al., 1993) (FIG. 5D). Furthermore, using gel shift analysis, we observed an increase in the complexes formed on a consensus AP-1 element using extracts from ΔFosB calvarial cultures. However, in the C2C12-derived stable cell lines, less binding to the same AP-1 element occurred with extracts from ΔFosB overexpressing cells than with extracts from control and Δ2ΔFosB overexpressing cells (FIG. 5E). These findings indicate that the effects of ΔFosB on osteogenesis and adipogenesis are most likely mediated by overexpression of the Δ2ΔFosB isoform. Antibody supershift analysis showed that in primary cultures (data not shown) and in transfected cells (FIG. 5F), the complexes associating with the AP-1 element mainly comprised FosB/ΔFosB, Fra-2 and JunD, which have been previously implicated in the regulation of osteoblast differentiation (McCabe et al., 1996) as well as Smad4, that has been recently shown to directly associate with AP-1 members (Liberati et al., 1999). Furthermore, this is consistent with previous work, which showed that JunD is the preferred partner for ΔFosB in brain (Chen et al., 1997).

Thus, Δ2ΔFosB levels are highest early in differentiation and promote expression of osteoblastic markers while repressing adipocytic differentiation. Given that members of the Fos family do not form homodimers, overexpression of ΔFosB isoforms may favor osteoblast commitment at the expense of adipogenesis through the formation of high affinity Δ2ΔFosB heterodimers, predominantly with JunD. Since Δ2ΔFosB is devoid of any known transactivation or repression domains, these complexes could act either as activators of transcription through their Jun partners or prevent the transcriptional activity of other AP-1 complexes by competing for binding to co-activators or to promoter-regulatory elements of genes responsible for commmitment to a particular lineage, or both. Interestingly, the promoters of several genes involved in osteoblast (Owen et al., 1990, Banerjee et al., 1996) and adipocytic (Distel et al., 1987, Stephen et al., 1992) differentiation include functional AP-1 binding sites. It was then determined whether ΔFosB and Δ2ΔFosB, which both lack the classical C-terminal transactivation domain of AP-1 family members but still contain the more controversial Fos Homology Domain (FHD), acted primarily as activators or repressors of transactivation. The stable cell lines were used in transient transactivation assays in order to compare the ability of ΔFosB and Δ2ΔFosB to activate or repress the activity of an osteocalcin (OG2) promoter/CAT reporter gene construct. Transfection of ΔFosB and Δ2ΔFosB with different concentrations of OG2-

CAT showed that both ΔFosB- and Δ2ΔFosB-expressing cells induced CAT expression 2-to 8- fold relative to mock-transfected cells, depending on the concentration of reporter plasmid used (data not shown). Thus, both the ΔFosB and the Δ2ΔFosB isoforms are capable of acting as transcriptional activators.

It has recently been suggested that adipocyte-secreted leptin acts as a negative regulator of bone formation via systemic regulation of osteoblasts by the hypothalamus (Ducy et al., 2000). Although a marked decrease in adipocytes in vitro and in vivo was observed in transgenic mice, and consequently a decrease in serum leptin (9.9±2.4 ng/ml vs 3.9±0.9 ng/ml, p<0.05), the possibility that the skeletal phenotype observed in ΔFosB transgenic mice resulted from the decreased levels of leptin can be excluded based on the following observations. First, the ΔFosB phenotype is cell autonomous and reproducible in vitro even after stable transfection of ΔFosB in the C2C12 cell line, i.e., in the absence of adipocytes. Second, Ducy et al. (2000) have shown that the effects of leptin cannot be mimicked in vitro and require the presence of the hypothalamus to affect osteoblast function. Third, although leptin is still present in our transgenic mice, the skeletal phenotype of osteosclerosis observed in ΔFosB transgenic mice is much more pronounced than the mild increases in bone formation found in leptin (ob/ob) or leptin receptor (db/db) deficient mice. Finally, of particular interest is the fact that a similar skeletal phenotype is described by Jochum et al. in mice overexpressing fra-1 under the control of the murine H2-K$^b$ class I MHC promoter (submitted jointly). Fra-1 is a closely related Fos family member which, as Δ2ΔFosB, has no known transcriptional activation domain. In this transgenic model, there are no apparent changes in body fat and/or adipocyte differentiation. Thus, the ability of ΔFosB and Fra-1 overexpression to increase bone formation in vitro and in vivo is cell autonomous and cannot be accounted for by changes in leptin levels.

Thus, overexpression of Fos family members which lack transcriptional domains while maintaining their DNA binding and heterodimerization properties, such as Δ2ΔFosB or Fra-1, induce a marked increase in bone formation which leads, in vivo, to osteosclerosis. Further understanding of the pathways involved in this anabolic response of the skeleton may help identify new targets for drug development.

Example 5

Method of Determining Whether a Test Agent Induces Bone Formation

All the transgenic mice are maintained in strict accordance with National Institutes of Health and institutional animal care guidelines. Transgenic mice TetOp-ΔFosB (Chen et al., 1998) are fed with water containing test agent and 5% sucrose. Expression of ΔFosB can be turned off with low doses of doxycycline or induced to very high levels in the absence of doxycyline. Thus, the test agent are administered in the absence and/or in the presence of doxycycline.

Luciferase Assay. Tissues from different organs are obtained by gross dissection. The tissues are homogenized using a sonicator or polytron. The homogenate is centrifuged for 5 min in a microfuge. Ten microliters of the supernatant is used for measurement of luciferase activity in a luminometer by use of the luciferase reporter gene assay kit (Boehringer-Mannheim Biochemicals, Indianapolis, Ind.). Luciferase activity is normalized to total protein concentration.

Western Blotting. One-dimensional Western blotting for ΔFosB is performed exactly as described by Chen et al. (1998), by using an anti-Fos-related antigen antibody (supplied by M. Iadarola, NIH, Bethesda, Md.) and chemiluminescence detection (Amersham, Arlington Heights, Ill.). Levels of ΔFosB immunoreactivity are quantified by measuring the optical density of specific bands using a Macintosh-based image analysis system with NIH image software.

Immunohistochemistry. Immunohistochemical analysis of ΔFosB is performed according to Chen et al. (1998). Transgenic mice are perfused with 4% paraformaldehyde-phosphate-buffered saline. Sections are labeled with a rabbit polyclonal anti-FosB antibody (1:5000; Santa Curz Biochemicals, Santa Cruz, Calif.). Immunoreactivity is detected by diaminobenzidine staining as described by Chen et al. (1998).

RT-PCR. Total RNA is isolated from striatum of transgenic mice using the RNAqueous phenol-free total RNA isolation kit (Ambion, Austin, Tex.) and poly(A)$^+$ is isolated using the Oligotex mRNA mini kit (Qiagen, Chatsworth, Calif.). One microgram of poly(A)$^+$ mRNA is used as template for cDNA synthesis using the Marathon cDNA amplification kit (Clontech, Palo Alto, Calif.). PCR is carried out according to standard protocols from Clontech. PCR primer pairs are designed to distinguish expression of the transgene from the of the endogenous gene. By use of a FosB primer (5' CAG TCT CAG TAC CTG TCT TC 3', SEQ ID NO: 2) and an SV40 primer (5' GTC AGC AGT AGC CTC ATC ATC ACT 3', SEQ ID NO: 3), it is possible to detect expression of the FosB transgene, which contain both FosB and SV40 sequences.

Histomorphometric and biochemical analyses as described under Materials and Methods can also be performed on these transgenic mice. Primary murine calvarial cells can also be obtained from the transgenic mice and analyzed as described under Materials and Methods. Other assays that are known to the skilled artisan can also be performed to determine whether the test agent modulates bone formation.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

References for Which a Complete Citation is not Provided in the Text of the Specification Anderson, R., Woodbury, D. & Jee, W. Humoral and ionic regulation of osteoclast acidity. *Calcif. Tissue Int.* 39, 252–258 (1986).

Aoki, K., DiDomenico, E., Sims, N. A., et al. They tyrosine phosphatase SHP-1 is a negative regulator of osteoclastogeneisis and osteoclast resorbing activity: increased resorption and osteopenia in me$_v$/me$_v$ mutant mice. *Bone* 25, 261–267 (1999).

Arneet, R. & Dempster, D. The effect of pH on bone resorption by rat osteoclasts in vitro. *Endocrinology* 119, 119–124 (1986).

Banerjee, C., Stein, J. L., van Wijnen, A. J., et al. TGF-β1 response in the rat osteocalcin gene is mediated by an AP-1 binding site. *Endocrinology* 137, 1991–2000 (1996).

Baron, R., Vignery, A., Neff, L., Silverglate, A. & Maria, A. S. in *Bone histomorphometry: Technique and interpretation* (ed Recker, R. R.) Vol. 1, 13–35 (CRC Press, Boca Raton, Fla., 1983).

Bellows, C. G., Heersche, J. N. M. & Aubin, J. E. Determination of the capacity for proliferation and differentiation of osteoprogenitor cells in the presence and absence of dexamethasone. *Developmental Biol.* 140, 132–138 (1990).

Bellows, C. G., Wang, Y. -H., Heersche, J. N. M. & Aubin, J. E. 1,25-dihydroxyvitamin D3 stimulates adipocyte differentiation in cultures of fetal rat calvaria cells: comparison with the effects of dexamethasone. *Endocrinology* 134, 2221–2229 (1994).

Beresford et al., Journal of Cell Science, 102, 341–351 (1992)

Cao, Z., Umek, R. M. & McKnight, S. L. Regulated expression of three C/EBP isoforms during adipose conversion of 3T3-L1 cells. *Genes Dev* 5, 1538–1552 (1991).

Chen, J., Kelz, M. B., Zeng, G., et al. Transgenic animals with inducible, targeted gene expression in brain. *Mol. Pharmacol.* 54, 495–503 (1998).

Chen, J., Kelz, M. B., Hope, B. T., Nakabeppu, Y. & Nestler, E. J. Chronic Fos-related antigens: stable variants of ΔFosB induced in brain by chronic treatments. *J Neurosci* 17, 4933–4941 (1997).

Distel, R. J., Ro, H. S., Rosen, B. S., Groves, D. L. & Spiegelman, B. M. Nucleoprotein complexes that regulate gene expression in adipocyte differentiation: direct participation of c-fos. *Cell* 49, 835–844 (1987).

Dorheim, M. A., Sullivan, M., Dandapani, V., et al. Osteoblastic gene expression during adipogenesis in hematopoietic supporting murine bone marrow stromal cells. *J Cell Physiol* 154, 317–328 (1993).

Ducy, P., Desbois, C., Boyce, B., et al. Increased bone formation in osteocalcin-deficient mice. *Nature* 382, 448–452 (1996).

Ducy, P., Amling, M., Takeda, S., et al. Leptin inhibits bone formation through a hypothalamic relay: a central control of bone mass. *Cell.* 100, 197–207 (2000).

Franzoso, G., Carlson, L., Xing, L., et al. Requirement for NF-κB in osteoclast and B-cell development. *Genes & Dev.* 11, 3482–3496 (1997).

Gimble et al., Journal of Cellular Biochemistry, 58, 393–402 (1995)

Grigoriadis, A. E., Shellander, K., Wang, Z-Q. & Wagner, E. F. Osteoblasts are target cells for transformation in c-fos transgenic mice. *J. Cell Biol.* 122, 685–701 (1993).

Gruda, M. C., van Amsterdam, J., Rizzo, C. A., Durham, S. K., Lira, S. & Bravo, R. Expression of FosB during mouse development: normal development of FosB knockout mice. *Oncogene* 12, 2177–2185 (1996).

Hayman, A. R., Jones, S. J., Boyde, A., et al. Mice lacking tartrate-resistant acid phosphatase (Acp 5) have disrupted endochondral ossification and mild osteopetrosis. *Development* 122, 3151–3162 (1996).

Johnson, R. S., Spiegelman, B. M. & Papaioannou, V. Pleiotropic effects of a null mutation in the c-fos proto-oncogene. *Cell* 71, 577–586 (1992).

Kelz, M. B., Chen, J., Carlezon, Q. A., et al. Expression of the transcription factor ΔFosB in the brain controls sensitivity to cocaine. *Nature* 401, 272–276 (1999).

Liberati, N., Datto, M. B., Frederick, J. P., et al. Smads bind directly to the Jun family of AP-1 transcription factors. *Proc. Natl. Acad. Sci. USA* 96, 4844–4849 (1999).

Marks, S. C., Jr. & Lane, P. W. Osteopetrosis, a new recessive skeletal mutation on chromosome 12 of the mouse. *J. Heredity* 67, 11–18 (1976).

McCabe, L. R., Banerjee, C., Kundu, R., et al. Developmental expression and activities of specific Fos and Jun proteins are functionally related to osteoblast maturation: Role of Fra-2 and Jun D during differentiation. *Endocrinology* 137, 4398–4408 (1996).

Nakabeppu, Y. & Nathans, D. A naturally occurring truncated form of FosB that inhibits Fos/Jun transcriptional activity. *Cell* 64, 751–759 (1991).

Nestler et al., Brain Research, 835, 10–17 (1999)

Owen, T. A., Bortell, R., Yocum, S. A., et al. Coordinate occupancy of AP-1 sites in the vitamin D-responsive and CCAAT box elements by Fos-Jun in the osteocalcin gene: Model for phenotype suppression of transcription. *Proc Natl Acad Sci USA* 87, 9990–9994 (1990).

Parfitt, A. M., Drezner, M. K., Glorieux, F. H., et al. Bone histomorphometry: Standardization of nomenclature, symbols, and units. Report of the ASBMR histomorphometry nomenclature committee. *J Bone Miner Res* 2, 595–610 (1987).

Quarles, L. D., Yohay, D. A., Lever, L. W., Caton, R. & Wenstrup, R. J. Distinct proliferative and differentiated stages of murine MC3T3-E1 cells in culture: an in vitro model of osteoblast development. *J. Bone Miner. Res.* 7, 683–692 (1992).

Sabatakos, G., Davies, G. E., Grosse, M., Cryer, A. & Ramji, D. P. Expression of the genes encoding CCAAT-enhancer binding protein isoforms in the mouse mammary gland during lactation and involution. *Biochem J* 334, 205–210 (1998).

Sambrook, J. Fritsch, E. F. & Maniatis, T. *Molecular Cloning: A Laboratory Manual* (Cold Spring Harbor Laboratory Press, New York, 1989).

Schreiber, E., Matthias, P., Muller, M. M. & Schaffner, W. Rapid detection of octamer binding proteins with 'mini-extracts', prepared from a small number of cells. *Nucleic Acids Res* 17, 6419 (1989).

Seifert, M. F. & Marks, S. C. Morphological evidence of reduced bone resorption in the osteosclerotic (oc) mouse. *Am J Anat* 172, 141–153 (1985).

Simonet, W. S., Lacey, D. L., Dunstan, C. R., et al. Osteoprotegerin: A novel secreted protein involved in the regulation of bone density. *Cell* 89, 309–319 (1997).

Soriano, P., Montgomery, C., Geske, R. & Bradley, A. Targeted disruption of the c-src proto-oncogene leads to osteopetrosis in mice. *Cell* 64, 693–702 (1991).

Stephens, J. M., Butts, M. D. & Pekala, P. H. Regulation of transcription factor mRNA accumulation during 3T3-L1 preadipocyte differentiation by tumour necrosis factor-alpha. *J. Mol. Endocrinol.* 9, 61–72 (1992).

Takahashi, N., Yamana, H., Yoshiki, S., et al. Osteoclast-like cell formation and its regulation by osteotropic hormones in mouse bone marrow cultures. *Endocrinology* 122, 1373–1382 (1988).

Tondravi, M. M., McKercher, S. R., Anderson, K., et al. Osteopetrosis in mice lacking haematopoietic transcription factor PU.1. *Nature* 386, 81–84 (1997).

Wang, Z-Q., Liang, J., Schellander, K., Wagner, E. F. & Grigoriadis. A. E. c-fos-induced osteosarcoma formation in transgenic mice: cooperativity with c-jun and the role of endogenous c-fos. *Cancer Research* 55, 6244–6251 (1995).

Wang, Z. -Q., Ovitt, C., Grigoriadis, A. E., Mohle-Steinlein, U., Ruther, U. & Wagner, E. F. Bone and haematopoietic defects in mice lacking c-fos. *Nature* 360, 741–745 (1992).

What is claimed is:

1. A method of identifying genes associated with osteogenesis or adipogenesis that are modulated by ΔFosB comprising (a) inducing ΔFosB in a cell associated with osteogenesis or adipogenesis; and (b) determining which genes associated with osteogenesis or adipogenesis are differentially expressed in said cell, thereby identifying genes that are modulated by ΔFosB.

2. The method of claim 1, wherein step (b) is performed using a yeast two-hybrid system or hybridization of cellular nucleic acids to a DNA chip.

3. The method of claim 1, wherein the cell is an in vitro cell.

4. The method of claim 3, wherein the cell is selected from the group consisting of calvarial cell, osteoblast, osteoclast, chondrocyte, and pluripotent precursor cell.

5. The method of claim 4, wherein the osteoblast is selected from the group consisting of MC3T3-E1, C2C12, MG-63, U2OS, UMR106, ROS 17/2.8, and SaOS2.

6. The method of claim 3, wherein the method further comprises obtaining cell lysates from the in vitro cell for determining which genes are differentially expressed.

7. The method of claim 3, wherein the method further comprises obtaining nuclear extracts from the in vitro cell for determining which genes are differentially expressed.

8. The method of claim 1, wherein inducing ΔFosB comprises exposing the cell to an agent selected from the group consisting of cocaine, amphetamine, nicotine, opiate, antidepressant, and antipsychotic agent.

9. The method of claim 1, wherein the cell is an in vivo cell.

10. The method of claim 1, wherein the cell is in an animal.

11. The method of claim 10, wherein the animal is a transgenic animal.

12. The method of claim 1, wherein the method is performed in a high throughput format.

13. The method of claim 1, wherein the method is performed using a DNA chip.

14. The method of claim 1, wherein step (b) comprises isolating RNA from the cell.

15. The method of claim 14, wherein step (b) comprises obtaining an RNA expression pattern.

16. The method of claim 15, wherein the RNA expression pattern is obtained using a DNA chip, Northern analysis, RT PCR, RNase protection, or subtractive hybridization.

17. A method of claim 3, wherein the cell is selected from the group consisting of adipocyte and preadipocyte.

18. A method of claim 17, wherein the adipocyte is selected from the group consisting of 3T3 F422 A, and ob 1771.

19. A method of claim 18, wherein the preadipocyte is 3T3-L1 preadipocyte.

20. A method of identifying genes associated with osteogenesis or adipogenesis that are modulated by ΔFosB comprising (a) inducing ΔfosB in a cell culture, wherein the cells are associated with osteogenesis or adipogenesis; and (b) determining which genes associated with osteogenesis or adipogenesis are differentially expressed in said cells, thereby identifying genes that are modulated by ΔFosB.

21. A method of claim 20, wherein the method is performed using cell lysates.

22. A method of claim 20, wherein the method is performed using nuclear extracts.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
gtcgacgtga gtcagcgcgc                                               20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide: FosB primer

<400> SEQUENCE: 2
cagtctcagt acctgtcttc                                               20

<210> SEQ ID NO 3
<211> LENGTH: 24
<212> TYPE: DNA
<213> ORGANISM: Artificial sequence
<220> FEATURE:
<223> OTHER INFORMATION: Synthetic oligonucleotide: SV40 primer

<400> SEQUENCE: 3
gtcagcagta gcctcatcat cact                                          24